United States Patent
Yap et al.

(10) Patent No.: US 10,295,462 B1
(45) Date of Patent: May 21, 2019

(54) DETECTION BY ACTIVE SPATIALLY AND SPECTRALLY STRUCTURED SENSING AND LEARNING (DAS4L)

(71) Applicant: HRL Laboratories, LLC, Malibu, CA (US)

(72) Inventors: Daniel Yap, Newbury Park, CA (US); Yuri Owechko, Newbury Park, CA (US); Richard M. Kremer, Ramona, CA (US); Shankar R. Rao, Agoura Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 13 days.

(21) Appl. No.: 15/445,782

(22) Filed: Feb. 28, 2017

Related U.S. Application Data

(60) Provisional application No. 62/302,621, filed on Mar. 2, 2016.

(51) Int. Cl.
*G01J 5/02* (2006.01)
*G01N 21/39* (2006.01)
(Continued)

(52) U.S. Cl.
CPC ............. *G01N 21/39* (2013.01); *G01N 21/27* (2013.01); *G01N 21/31* (2013.01); *G01N 21/3563* (2013.01); *G01N 2201/1293* (2013.01)

(58) Field of Classification Search
CPC ...... G01N 21/27; G01N 21/55; G01N 21/314; G01N 21/39; G01N 21/3563;
(Continued)

(56) References Cited

U.S. PATENT DOCUMENTS 5,790,242 A 8/1998 Stern et al.
6,822,742 B1 * 11/2004 Kalayeh ................ G01N 21/31
250/338.1
(Continued)

OTHER PUBLICATIONS

Ouerghemmi et al., "Applying blind source separation on hyperspectral data for clay content estimation over partially vegetated surfaces," 2011, Geoderma, vol. 163, pp. 227-237.*
(Continued)

*Primary Examiner* — Kiho Kim
(74) *Attorney, Agent, or Firm* — Ladas & Parry

(57) ABSTRACT

A sensor system including a spectrometer with a light source having a plurality of selectable wavelengths, a controller for controlling the sensor system, for selecting wavelengths of illumination light produced by the light source, and for controlling the light source to illuminate a spatial location, a photodetector aligned to detect light received from the spatial location, a blind demixer coupled to the photodetector for separating received spectra in the detected light into a set of sample spectra associated with different demixed or partially demixed chemical components, a memory having a plurality of stored reference spectra, a non-blind demixer coupled to the blind demixer and to the memory for non-blind demixing of the sample spectra using the reference spectra, and a classifier coupled to the non-blind demixer for classifying the set of demixed sample spectra into chemical components using the reference spectra.

23 Claims, 18 Drawing Sheets

(51) Int. Cl.
*G01N 21/3563* (2014.01)
*G01N 21/31* (2006.01)
*G01N 21/27* (2006.01)

(58) Field of Classification Search
CPC ... G01N 2201/1293; G01N 21/31; G01J 3/26; G01J 3/027; G01S 17/89; G01S 7/4802; G01V 8/02
See application file for complete search history.

(56) References Cited

U.S. PATENT DOCUMENTS

| | | | |
|---|---|---|---|
| 9,230,302 | B1 | 1/2016 | Owechko et al. |
| 2005/0271258 | A1 | 12/2005 | Rowe |
| 2006/0038705 | A1 | 2/2006 | Brady et al. |
| 2007/0242327 | A1 | 10/2007 | Powell et al. |
| 2008/0106983 | A1 | 5/2008 | Takemoto et al. |
| 2011/0270092 | A1 | 11/2011 | Kang et al. |
| 2011/0279682 | A1 | 11/2011 | Li et al. |
| 2013/0012794 | A1 | 1/2013 | Zeng et al. |
| 2013/0271752 | A1* | 10/2013 | Bellian ............... G01N 21/27 356/73 |
| 2014/0009752 | A1 | 1/2014 | Cronin et al. |
| 2014/0247372 | A1 | 9/2014 | Byren |
| 2015/0186754 | A1* | 7/2015 | Paauw ............... H01J 49/0036 382/224 |
| 2015/0205992 | A1 | 7/2015 | Rowe |
| 2016/0290927 | A1 | 10/2016 | Buczkowski et al. |

OTHER PUBLICATIONS

Li et al., "A survey on represetation-based classification and detection in hyperspectral remote sensing imagery," 2016, Pattern Recognition Letters, vol. 83, pp. 115-123.*
Abbas, Chan and Yee, "A dual-detector optical heterodyne receiver for local oscillator noise suppression," Journal of Lightwave Technology, 3(5), 1110 (Oct. 1985).
Aharon, Elad, and Bruckstein, "The K-SVD: An Algorithm for Designing of Overcomplete Dictionaries for Sparse Representation", the IEEE Trans. on Signal Processing, vol. 54, No. 11, pp. 4311-4322, Nov. 2006.
Castro-Suarez, Pollock and Hernandez-Rivera, "Explosives detection using quantum cascade laser spectroscopy," Proceedings SPIE vol. 8710, paper 871010 (2013).
Fuchs, et al., "Imaging standoff detection of explosives using widely tunable midinfrared quantum cascade lasers," Optical Engineering, 49(11), 111127 (Nov. 2010).
Goyal, et al., "Dispersion-compensated wavelength beam combining of quantum-cascade-laser arrays," Optics Express, 19(27), 26725 (Dec. 2011).
Itsuno, Phillips and Velicu, "Predicted performance improvement of Auger-suppressed HgCdTe photodiodes and p-n heterojunction detectors," IEEE Transactions on Electron Devices, 58(2), 501 (Feb. 2011).
Larcom and Coffman, "Foveated Image Formation through Compressive Sensing," Image Analysis & Interpretation (SSIAI), 2010 IEE Southwest Symposium. May 23-25, 2010, Austin, TX, USA, pp. 145-148.
Lee, et al., "Beam combining of quantum cascade laser arrays," Optics Express, 17(18), 16216 (2009).
Lee, et al., "DFB quantum cascade laser arrays," IEEE Journal of Quantum Electronics, 45(5), 554 (May 2009).
Menzel, et al., "Quantum cascade laser master-oscillator power-amplifier with 1.5 W output power at 300 K," Optics Express, 19(17), 16229 (2011).
Phillips and Bernacki, "Hyperspectral microscopy of explosives particles using an external cavity quantum cascade laser," Optical Engineering, 52(6), 061302 (Jun. 2013).
Sharma and Nayak, "Region of Interest Compressed Sensing," ISMRM Workshop on Data Sampling and Image Reconstruction, Jan. 2009, Sedona.
Slivken, et al., "Sampled grating, distributed feedback quantum cascade lasers with broadband tenability and continuous operation at room temperature," Applied Physics Letters, v.100, 261112 (2012).
Suter, B. Bernacki and Phillips, "Spectral and angular dependence of mid-infrared diffuse scattering from explosives residues for standoff detection using external cavity quantum cascade lasers," Applied Physics B, 108:965-974, Sep. 15, 2012.
Wijewarnasuriya, "Nonequilibriium operation of long wavelength HgCdTe photo detectors for higher operating temperatures," Proceedings SPIE vol. 7780, 77800A (2010).
Zelnik-Manor, Rosenblum, Eldar and, "Sensing Matrix Optimization for Block-Sparse Decoding." IEEE Transactions on Signal Processing 59(9): 4300-4312 (Sep. 2011).
"LaserSense™: Compact Gas Detection System," webpage available at: http://www.blockeng.com/products/lasersense.html, accessed on Sep. 23, 2016 at 10:29 AM.
"LaserWarnTM: Open-Path Chemical Detection System" webpage available at: http://www.blockeng.com/products/laserwarn.html, accessed on Sep. 21, 2016 at 3:25 PM.
"LaserTune™ Widely Tunable Mid-Infrared Laser Source" webpage available at: http://www.blockeng.com/products/lasertune.html, accessed on Sep. 21, 2016 at 3:28 PM.
"Ultra-broadly tunable mid-IR external-cavity CW/Pulsed MIRcatTM laser system" product brochure, Feb. 29, 2016, available at: http://www.daylightsolutions.com/scientific-instruments/sci-products/sci lasers/mircat.htm, accessed on Sep. 21, 2016.
"OmniLux™ Multiple Tunable QCL System" webpage available at http://www.pranalytica.com/products-services/omnilux.php, accessed on Sep. 21, 2016 at 3:47 PM.
J. R. Quinlan in tutorials and references available at URL: http://www.ruleguest.com visited on Feb. 24, 2017.
From U.S. Appl. No. 15/280,575 (unpublished) Application and Office Actions.
From U.S. Appl. No. 15/283,358 (unpublished) Application and Office Actions.
From U.S. Appl. No. 15/275,172 (unpublished) Application and Office Actions.
From U.S. Appl. No. 14/204,028 (now U.S. Pat. No. 9,230,302) Notice of Allowance dated Aug. 28, 2015.
U.S. Appl. No. 15/275,172, filed Sep. 23, 2016, Yap et al.
U.S. Appl. No. 15/280,575, filed Sep. 29, 2016, Owechko et al.
U.S. Appl. No. 15/283,358, filed Oct. 1, 2016, Rao et al.
Choi et al. in Blind Source Separation and Independt Component Analysis, Neural Information Processing—Letters and Review vol. 6, No. 1, Jan. 2005.
J. F. Cardoso and A. souloumiac in "Blind beamforming for non-Gaussian signals," IEE Proceedings—F v. 140, n. 6, Dec. 1993, p. 362.
From U.S. Appl. No. 15/275,172 (unpublished) Non-Final Office Action dated Jun. 20, 2017.

* cited by examiner

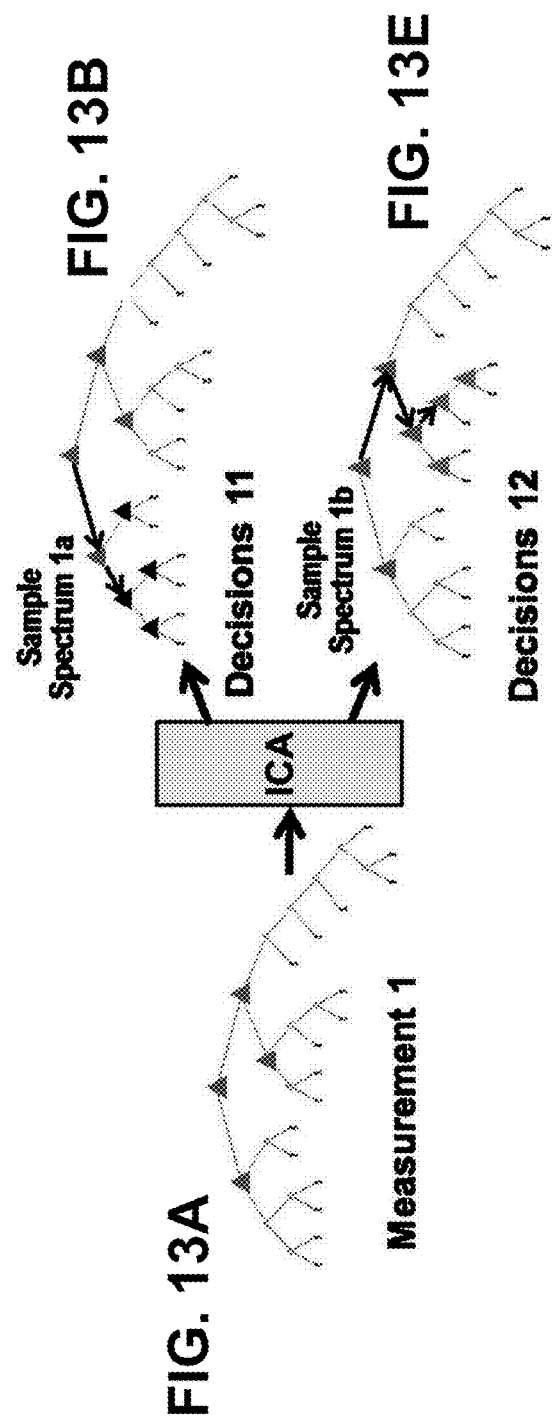

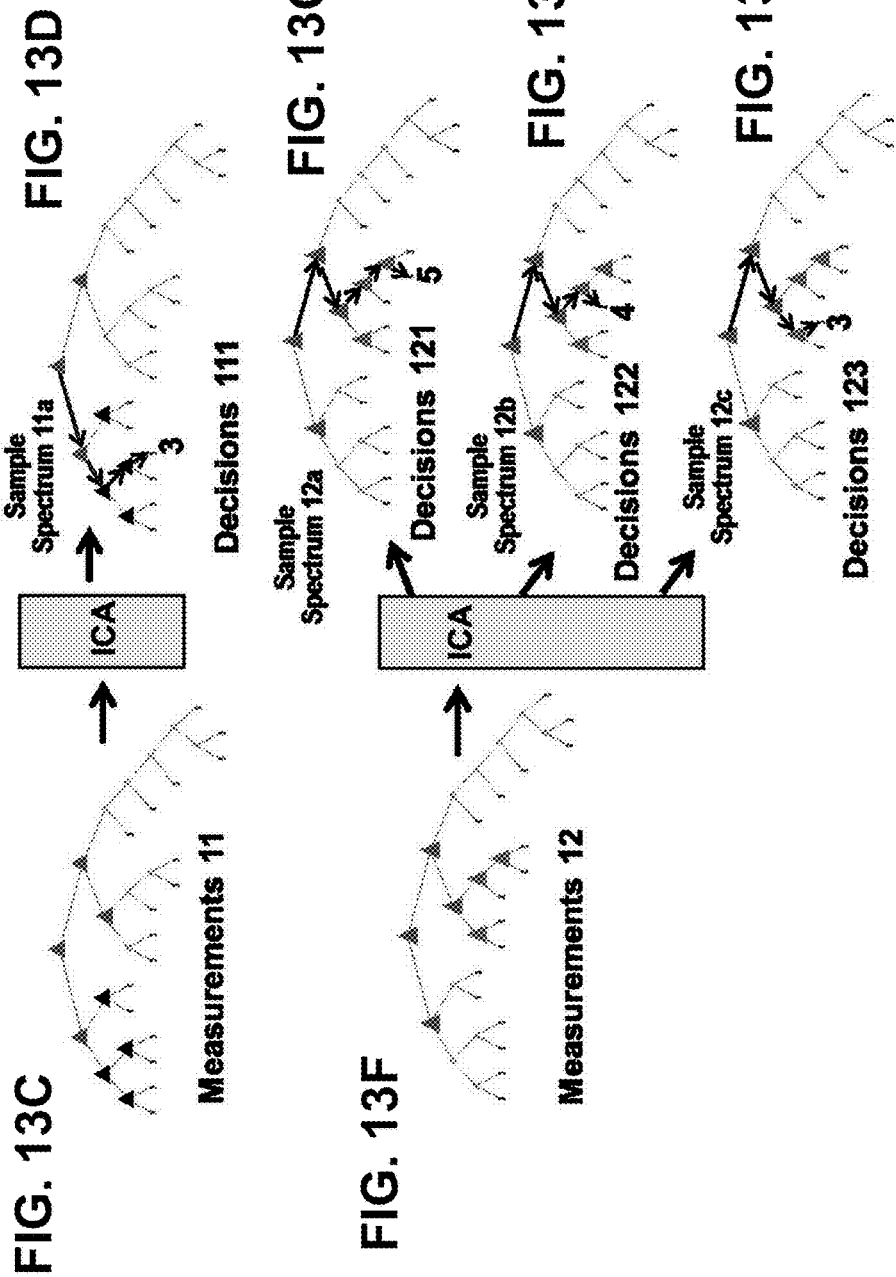

DETECTION BY ACTIVE SPATIALLY AND SPECTRALLY STRUCTURED SENSING AND LEARNING (DAS4L)

CROSS REFERENCE TO RELATED APPLICATIONS

This application relates to U.S. patent application Ser. No. 15/275,172, filed Sep. 23, 2016, U.S. patent application Ser. No. 15/280,575, filed Sep. 29, 2016, U.S. patent application Ser. No. 15/283,358, filed Oct. 1, 2016, and U.S. Pat. No. 9,230,302, issued on Jan. 5, 2016, and relates to and claims the benefit of priority from U.S. Provisional Patent Application 62/303,621, filed Mar. 2, 2016, which are incorporated herein by reference as though set forth in full.

STATEMENT REGARDING FEDERAL FUNDING

None.

TECHNICAL FIELD

This disclosure relates to sensors and active spectrometers.

BACKGROUND

Chemical species can be identified by the characteristic features in their infrared absorption and/or transmission spectrum. For light in the mid-infrared (MIR) spectral region of 350-4,000 $cm^{-1}$, many molecules have characteristic vibrational and rotational energy states that can be populated upon interaction with photons of the appropriate energy (or wavenumber) resulting in absorption and possibly enhanced reflection of light at those specific wavenumbers. This wavenumber specific absorption and enhanced reflection enables the detection of trace amounts of those chemicals by measuring the intensities at various wavenumbers of the light back-scattered from a surface covered by a residue of the chemicals. The back-scattered light can result from the absorption and enhanced reflection processes, which are described by the imaginary part of the residue material's refractive index. The back-scattered light also arises from reflection of light as described by the real part of the material refractive index, including both the light reflected from the various surfaces of the residue and also the light transmitted through the residue and reflected from the underlying substrate surface.

A laser-illuminated active spectrometer can be used to detect and identify chemical residues that may be located on distant surfaces. Chemicals such as highly energetic materials (HEM) have many of their spectral "fingerprint" features within the long-wave infrared (LWIR) spectral range of 800 $cm^{-1}$ to 1600 $cm^{-1}$ for which quantum cascade lasers have been demonstrated. These laser sources enable a residue-covered surface to be probed at large stand-off distances because the optical beams formed from the laser outputs can have low-divergence and high power. Also, light from these laser sources can be focused onto small spots, resulting in laser illumination of high brightness and thus higher signal levels for the spectra of the back-scattered light.

Many surfaces, such as the exterior of a vehicle, are highly curved. Thus, a spatially fixed laser source would illuminate those surfaces at a variety of tilt angles, with many of those angles being far from normal incidence (which is perpendicular to the surface). If a detector of the back-scattered light is co-located with or located close to the laser source, the amount of back-scattered light returned to the detector can be very low. For example, the detected back-scattering for relative tilt angles of the surface larger than 5° can be $10^{-3}$ to $10^{-5}$ that of the signal detected for 0° tilt. Thus, it is beneficial to maximize the power or intensity of the laser illumination to increase the signal. However, the allowable or achievable laser intensity is limited in many cases. In many applications, the laser power must be below the eye-safety limit, which is 0.1 Watts/$cm^2$ for continuous illumination with MIR light. The eye-safety limited laser power can be used more effectively by illuminating the probed surface with only those wavenumbers that are especially relevant for the spectroscopic determination of the chemical species, such as those specific wavenumbers associated with the spectral "fingerprint" features of the chemicals that may or are expected to comprise a residue on the surface.

In the LWIR spectral range, there can be substantial thermal or black-body emission of radiation from many surfaces, including the surface being probed. To reduce the effects of this additional radiation on the spectra detected by the sensor, it is beneficial for the sensor system to collect and couple to its photodetector only the light from the spatial spot on the surface that is being illuminated by the laser source probing that surface. The disclosed framework can control both the location of the laser-probed spot and the location of the spot observed by the photo-detector.

In many cases, the residue on a surface covers only a relatively small portion of the overall surface. Also, there often can be several patches of residue that contain the chemicals of interest, with the areas between the patches not covered with any residue or not covered with those chemicals of interest. A given patch of residue often is spatially continuous and is separated from another patch of residue by residue-free areas of the surface, much like islands in the sea. When the size of the laser-probed spot is smaller than a residue patch, the disclosed sensor system can direct that spot to either be within a residue patch or be in a residue-free portion of the overall surface, which is beneficial for analyzing spectra arising from mixtures of chemical components.

A residue can comprise a mixture of multiple chemicals and the surface itself can contain multiple chemicals. The relative amounts of the chemical species in a mixture typically can be different for different spatial spots of the residue and the thickness of the residue also can vary from spot to spot. Different residue patches can contain different mixtures of chemicals. Each chemical has a unique characteristic spectrum and the materials comprising the surface likewise have their unique spectra. Also, the back-scattering spectra obtained even for a single chemical can vary with the thickness of the residue, the concentration of the chemical, the reflectance of the underlying surface, the roughness of the surface, the roughness of the residue, and the tilt angle. For example, the back-scattering spectrum could resemble the reflectance spectrum of the chemical species in some cases but resemble the transmittance spectrum (or the inverse of the absorbance spectrum) in other cases. The disclosed sensor system framework makes use of this spectral variation and also of the spatial structure of the residue-covered surface to facilitate the selection of the wavenumbers in the illuminating light and also the detection and identification of the chemicals in the residue patches and in the residue-free surface.

U.S. Pat. No. 9,230,302, which is incorporated herein by reference, describes a Foveated Compressive Sensing System for acquiring and reconstructing an optical image. This system makes use of prior knowledge about the image data or about the task to be performed with the imagery to determine the spatial points of the data to be measured and/or retained or the forms used to represent the image data. The resulting image has certain spatial regions that are represented with high information-content, such as high spatial resolution. These regions are called the "regions of interest" (ROI). Other spatial regions of the image are represented with much lower information content. The prior knowledge is used to determine and define the ROI.

In one example, the prior art Foveated Compressive Sensing System operates in a global measurement mode and gathers scene-specific information, such as the intensity of light at observed locations of the scene and the spatial patterns in that intensity distribution, from the entire observed portion of the scene and determines the spatial ROI. This global measurement is done with low spatial resolution. The system is then used in a local "foveated" measurement mode in order to focus the measurement and representation resources on the spatial ROI and on the task-relevant features in those ROI. The "foveated" measurements can provide much higher effective spatial resolution for the portion of the image within the ROI. The system can be switched alternately between global and local measurement modes as required to perform an imaging, recognition or tracking task. Compared to conventional compressive-sensing methods, in which the spatial measurements are made in a random manner, the task-aware sampling of the scene done by this prior art system can reduce the physical number of measurements needed to achieve a given level of task performance.

The present disclosure sensor system is similar to the prior art Foveated Compressive Sensing System in that it likewise makes use of knowledge about the task and the scene to define and determine spatial regions of interest (ROI). However, in the present disclosure it is the spectral resolution that is enhanced within these spatial ROI. Also, the signal-to-noise ratio can be higher for the measured spectra associated with these ROI, since higher illumination power can be applied at each illuminated spectral wavenumber or wavelength when fewer spectral points are illuminated simultaneously.

Most prior art spectrometric sensors make use of ambient illumination or broadband light sources, such as a Globar™ source, and cannot actively control the wavelengths or wavenumbers of the illuminating light. Some prior art spectrometric sensors make use of tunable laser sources for which a physical tuning element, such as a grating, is moved to scan the wavenumber of the emitted light continuously over some spectral span. With such laser sources, it is difficult to hop the wavenumber of the light arbitrarily from one value to another, and that kind of wavenumber or wavelength hopping is not done in practice. The present disclosure framework makes use of laser sources that provide arbitrary hopping of the laser emission from one selected value to the next, and that can emit multiple selected wavelengths simultaneously.

What is needed is an improved spectral sensor system and method. The embodiments of the present disclosure answer these and other needs.

SUMMARY

In a first embodiment disclosed herein, a sensor system comprises a spectrometer with a light source having a plurality of selectable wavelengths, a controller for controlling the sensor system, for selecting wavelengths of illumination light produced by the light source, and for controlling the light source to illuminate a spatial location, a photodetector aligned to detect light received from the spatial location, a blind demixer coupled to the photodetector for separating received spectra in the detected light into a set of sample spectra associated with different demixed or partially demixed chemical components, a memory having a plurality of stored reference spectra, a non-blind demixer coupled to the blind demixer and to the memory for non-blind demixing of the sample spectra using the reference spectra, and a classifier coupled to the non-blind demixer for classifying the set of demixed sample spectra into chemical components using the reference spectra.

In another embodiment disclosed herein, a method for detecting and identifying chemical components comprises illuminating a plurality of locations with light having a first set of a plurality of wavelengths, measuring an intensity of back-scattered light from the first set of the plurality of wavelengths, using the measured intensity of the back-scattered light to make an intermediate identification of the chemical components, using the intermediate identification to determine at least a second set of a plurality of wavelengths for illuminating the plurality of locations, measuring an intensity of second back-scattered light from the second set of the plurality of wavelengths, and using the measured intensity of the second back-scattered light to make an identification of the chemical components, wherein the second set of the plurality of wavelengths has a finer spacing than the first set of a plurality of wavelengths These and other features and advantages will become further apparent from the detailed description and accompanying figures that follow. In the figures and description, numerals indicate the various features, like numerals referring to like features throughout both the drawings and the description.

BRIEF DESCRIPTION OF THE DRAWINGS

FIG. 11A shows spectra obtained after an exponential transformation, FIG. 11B shows binary spectra obtained after a subsequent thresholding operation, and FIG. 11C shows the prototype spectra at the higher-level nodes obtained after a subsequent exclusive-OR type operation on the underlying binary spectra shown in FIG. 11B in their sub-clusters in accordance with the present disclosure;

FIGS. 13A, 13B, 13C, 13D, 13E, 13F, 13G, 13H and 13I show decision trees used to select wavenumber measurement points and to determine the chemical components in a demixed sample spectrum in accordance with the present disclosure.

DETAILED DESCRIPTION

Figure 1:
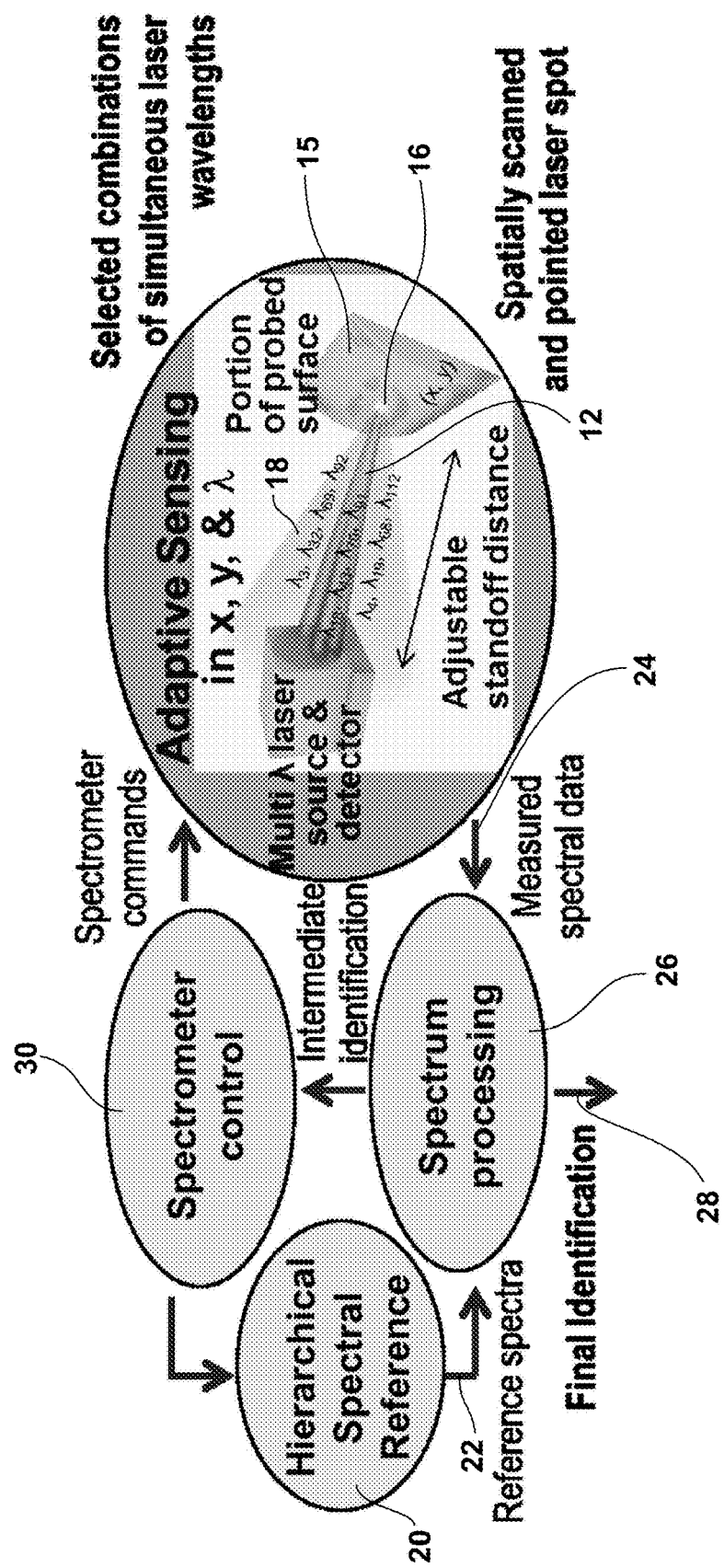
FIG. 1 shows a multi-wavelength actively illuminated, spatially probing spectrometer sensor system in accordance with the present disclosure.

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

The present disclosure describes an adaptive spectrometer-in-the-loop sensor system that detects and identifies chemical species based on their wavelength-dependent absorption and reflection of light. The active spectrometer of this sensor system can illuminate a target area with multiple simultaneous wavelengths (or wavenumbers) of light and can obtain and provide spatially dependent information on the relative amounts of light at those wavelengths that is back-scattered from the illuminated target area and collected by the spectrometer detector. The sensor controller controls a multi-wavelength laser illuminator and selects the combination of wavelengths emitted by the illuminator. The controller also selects a sequence of spots on a target surface to be probed by the sensor system and controls the pointing of one or more beams of multi-wavelength light onto those spots. The controller collects, from a multi-wavelength optical receiver in the spectrometer, measurements of multi-wavelength spectra that indicate the amount of light at each illumination wavelength that is reflected and/or back-scattered from the surface. The controller can store a copy of a multi-wavelength back-scatter measurement in a memory for access and processing at a later time.

The sensor system uses the reference spectra from a spectral-reference library to construct a structured organization of spectral-evaluation decisions—a decision tree that is trained by the reference spectra. The sensor controller executes algorithms to process the information in a collection of multi-wavelength back-scatter measurements to form a set of constituent spectra or de-mixed sample spectra. The controller executes an algorithm that uses the processed information to determine a group of spots on the target surface to be probed for the presence of certain chemicals and the combination of illumination wavelengths to be used in the probing of those spots. The controller selects one or more reference spectra from a spectral-reference library and executes algorithms to model the information in a multi-wavelength sampled pure spectrum or constituent spectrum of a mixture of chemicals as a weighted combination of the information in the selected reference spectra. The controller also executes an algorithm that uses the processed information together with a decision tree to determine the values of one or more likelihood measures that indicate the quality of an association between the probed spot and a reference spectrum stored in the spectral-reference library. The controller executes a control and processing loop that obtains one or more multi-wavelength measurements, processes the obtained multi-wavelength data, determines one or more likelihood values, and determines a location and a combination of wavelengths for subsequent probing. In some embodiments of the sensor system, this loop can be executed until a likelihood measure exceeds a given value, until a decision point is reached, or until a sensing time interval has been exceeded.

The sensor system can operate in a global survey mode in which an area of the target surface is probed with a broad range of illumination wavelengths that have a coarse spacing in wavelength. The sensor system also can operate in a local interrogation mode in which one or more selected spatial regions of interest (ROI) from the target surface are probed with selected combinations of illumination wavelengths that have a fine spacing in wavelength. In some embodiments, these illumination wavelengths can be grouped into spectral bands of interest (BOI), with each band typically including multiple closely spaced wavelengths. For example, surveys of selected, smaller-area regions of the target surface can be done for identified ROIs and, in some cases, with finer wavelength spacing. These spatial ROI surveys are then used to determine specific spectral BOI regions to measure with even higher spectral resolution.

In some embodiments, the sensor system organizes the reference spectra into a hierarchical branching structure for which each termination or leaf of the tree structure is associated with a reference spectrum. Those endmembers that share common branching points or nodes may be considered as being part of the same cluster or group. In some embodiments, this grouping is based on key distinguishing or salient spectral features of the reference spectra that occur at certain wavelengths. In some embodiments, this library also contains composite spectra that are produced by combining or merging the spectral information present in a cluster or group of several terminal reference spectra, or by combining or merging the spectral information present in a cluster or group of several other composite spectra. These composite spectra are associated with nodes that are higher in the hierarchical tree structure, with each node representing a branching point in the hierarchical structure. In some embodiments, the composite spectrum associated with a given node is used as a reference spectrum to provide an intermediate classification of the measured spectrum or of the de-mixed constituent spectrum. In some embodiments, the sensor system uses the reference spectra to construct and train a decision tree that comprises nodes or decision points. In prior spectral reference libraries, each reference spectrum is associated with only one termination of the hierarchical structure such that there is a one-to-one correspondence between termination and reference spectrum. In contrast to these prior art, the decision-tree, spectral-reference organization of the disclosed sensor system can have a given reference spectrum associated with multiple terminations of the hierarchical structure.

In some embodiments, the sensor system controller first performs sensor measurements and processes the spectral information from these measurements for the purpose of obtaining intermediate identification-estimates of chemicals based on library information described in higher levels of the hierarchical structure. The controller then uses these intermediate identification results to control the additional, second sensor measurements and the processing of spectral information that enable comparisons to be made with composite spectra or terminal reference spectra that are nested in layers further down in the structure. In some embodiments, the controller uses these intermediate identification results to select a cluster or group of one or more nodes that are at a lower level of the hierarchical structure than the node determining the first sensor measurements.

The integration of the spectrometer as part of a control, spectral processing and spectrum classification loop enables the sensor system to make efficient use of the laser illumination power, the computation resources and also the sensing-decision time. The power and time efficient operation is consistent with a sensor system that is portable and also a sensor system that acquires spectral measurements and makes sensing determinations in real time.

This sensor system can detect the presence of a given chemical based on its infrared backscatter/absorbance/reflectance/transmittance (BART) signature. Many chemicals such as explosives and highly energetic materials, chemical warfare agents and simulants, narcotics and other drugs, biological products, and industrial chemicals have characteristic backscattering, absorbance, reflectance or transmittance features at specific wavelengths (or wavenumbers) in the LWIR, MWIR and SWIR spectral ranges that can be used to identify the presence of those chemicals based on their infrared (IR) signatures. This sensor system can successively illuminate a sequence of small spots on a target surface and measure the infrared BART spectra associated with each illuminated spot. The sensor system can be used for standoff detection of chemicals on a probed surface or in the optical path between the surface and the sensor system. The sensor system also can produce a multi-spectral spatial map of the probed surface and/or volume. Different areas of the probed surface and/or volume can be probed with different combinations of illumination wavelengths.

Prior art sensors, such as the passive hyperspectral imagers, typically utilize illumination that has a broad and generally uniformly spread set of wavelengths of light. These prior sensors then measure the spectra for each point of the surface with the same spectral resolution and spatial resolution. Although in some cases of prior sensors, the processing of the spectral information can involve spatial regions of interest, so that not all of the measured data needs to be considered in the processing that accomplishes the chemical detection and identification, all of the measurements are still made. In contrast to the prior art, the present disclosure describes a system architecture and controller that enables the sensor system to make more efficient use of the illumination power and also the spectrum acquisition time by illuminating with and measuring only a selected subset of wavelengths that are adaptively selected based on earlier measurements.

The disclosed sensor system takes advantage of the inherent spatial and spectral structure of the BART spectra from chemical residues on surfaces to separate or de-mix components from mixtures of spectra. Those residues typically have limited and non-uniform spatial extent and the surface will thus contain spatially distinct residue-covered and residue-absent regions. Measurements of these regions provide sufficient information to separate out the spectra of target chemicals from spectral clutter typically obtained in measurements of mixtures of chemical residues and background material. The spectral structure is associated with the characteristic molecular rotational and vibrational energy states that are excited by the incident light of the appropriate wavenumber (or wavelength) and thus enhancing the absorption or the reflection of light at that wavenumber (or wavelength).

The disclosed sensor system can be used to remotely detect the condition of manufactured surfaces, such as the condition of paints being dried or composites and seams being cured, and the disclosed sensor system can be used to detect the presence and even the amount of contaminants on a manufactured surface. The disclosed sensor system can also be used to detect and measure gas-phase chemicals such as those produced by a manufacturing process. Thus, this sensor system can be useful for manufacture-process monitoring.

The disclosed sensor system integrates an active illumination spectrometer in a chemical detection and identification loop. In typical sensors, the spectral measurement is done first, separately from the chemical detection and identification function. Then, once a spectrum or a set of spectra is acquired, the chemical detection and identification algorithms are applied to the acquired spectra. Therefore, many or most of the measured spectral points or wavenumber values are never used for the identification. For the disclosed system, the sensor cycles repeatedly between steps of spectral measurement and steps of spectrum interpretation to achieve intermediate detection and identification. The intermediate identification results are then used to control subsequent spectral measurements whose acquired spectra are then interpreted, which results in measurements that are more efficient for identification.

The spectrometer-in-the-loop architecture is illustrated schematically in FIG. 1. The spectrometer can selectively illuminate a spatial location, which may be for example, a spot 16 on a probed surface 15 with beams of light 12 of multiple wavelengths ($\lambda_a, \lambda_c, \ldots \lambda_k$) and change the pattern of wavelengths as commanded by the sensor controller 30. The spatial location may also be not on a probed surface, for example, when the spatial location is within an atmosphere to sense chemical components in the atmosphere. The spectrometer also can move the spatial location (x, y) of the illuminated spot 16. The system makes use of a library 20 of reference spectra 22 and compares measured spectra data 24 with information obtained from the reference spectra 22 to perform spectrum processing 26 for obtaining chemical detection and identification 28. The sensor or spectrometer control 30, the hierarchical spectral reference 20 and the spectrum processing 26 may all be contained within the multi wavelength laser source and detector 10, as shown in FIG. 2.

Figure 2:
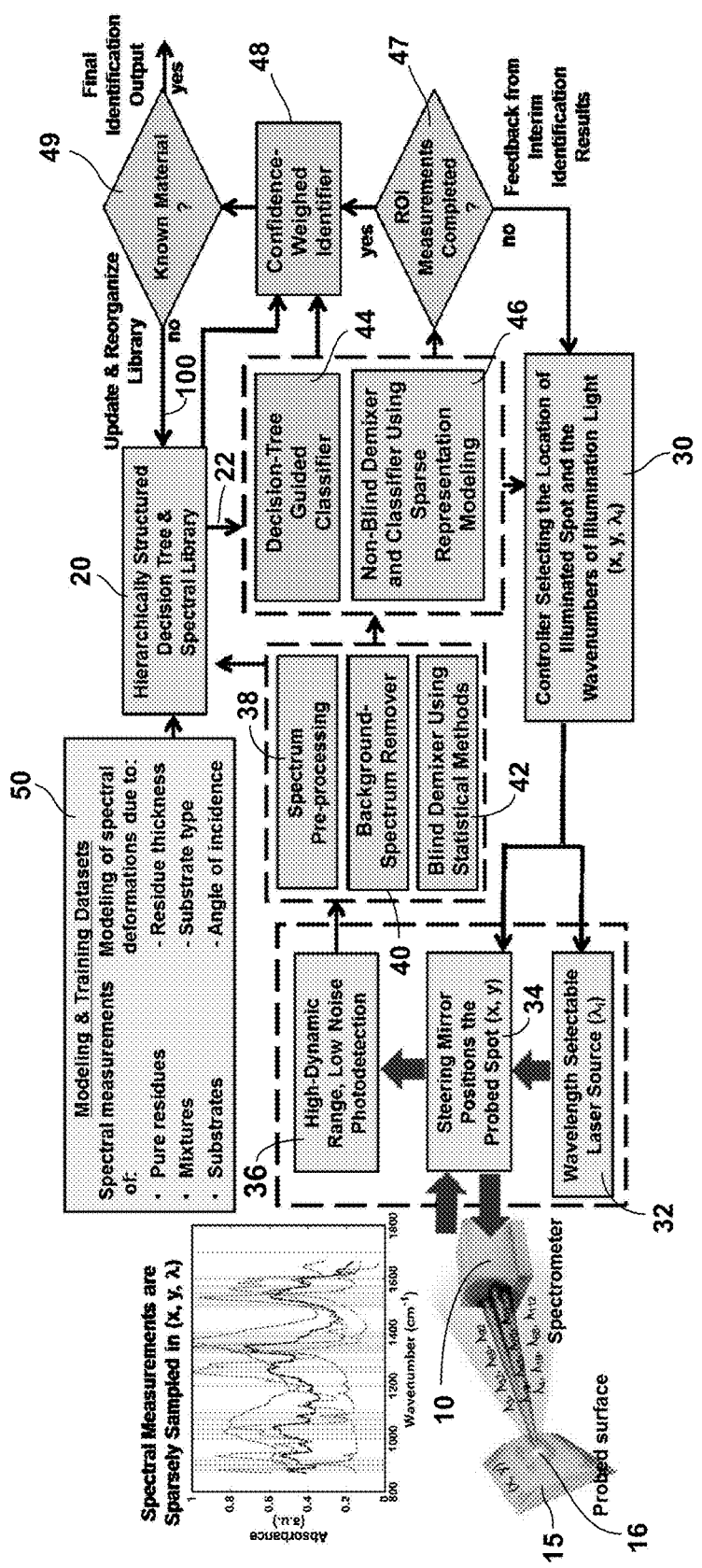
FIG. 2 shows a spectrometer-in-the-loop framework in accordance with the present disclosure.

FIG. 2 shows an example of the spectrometer-in-the-loop system and the key elements of that system. One key element is a controller 30 that determines the set of wavelengths or wavenumbers, which are the inverse of wavelengths, of the laser light 12 that the sensor 10 uses to illuminate a spot 16 on the probed surface 15. This controller 30 also determines the spatial location of the illuminated spot 16. For example, the controller 30 could select the values of the drive currents that control the wavelengths of the light 12 emitted by the laser source 32 in the spectrometer 10. Also, the controller 30 may select the values of the drive voltages that control an optical-beam steering mirror 34 in the spectrometer 10 that points the laser light 12 onto the probed surface 15 and that couples the light 18 back-scattered from that surface 15 onto a photodetector 36, which is a multi-wavelength light-detector in the spectrometer 10. The output of the light-detector 36 is a set of values that indicate the measured back-scattered light intensity at each of the illumination wavelengths. As discussed above, the spectral intensity pattern of the back-scattered light 18, i.e., the back-scatter spectrum, is indicative of the chemical composition of the materials in the probed spot 16.

In some applications, it is desirable to identify the specific chemical materials in the probed spot 16. In other applications, it may be sufficient to determine whether those materials are members of a class of chemicals, such as explosives or narcotics. Although these chemicals have specific chemical bonds and thus characteristic features in their back-scatter spectrum, such as peaks or dips occurring at a particular wavenumber value, other chemicals of a different class also could have some of the same spectral features. Thus, to sufficiently identify a chemical that may be in a probed spot 16, it often is necessary to compare many wavenumber points of a measured spectrum with a reference spectrum 22 that is obtained for a pure sample of the chemical that is not mixed with other chemical species. The disclosed framework also includes memory 20, which stores the spectral library 20 that is derived from these reference spectra 22. Spectral information supplied to and stored in the library 20 can be obtained from modeling and training datasets 50 that can include measurements of pure chemical residues, from mixtures containing several chemical species, and from substrate materials (that are representative of the surfaces containing the residues). The modeling datasets 50 may also include spectral deformations that may result from various measurement conditions, such as angle of incidence of the probe light 12, residue thickness and substrate conditions, such as texture. These provide additional information or reference spectra 22 for the library 20. The spectral library 20 may be organized as a hierarchically structured library 20 that facilitates not only the detection and identification of the chemicals but also the measurements performed by the spectrometer. In some embodiments, the hierarchical structure 20 can take the form of a decision tree with nodes that correspond to decision or evaluation points. In some embodiments, the hierarchical structure can take the form of a hierarchical clustered organization with nodes that represent groupings or clusters of spectra having similar characteristics.

In many cases, the residue can contain a mixture of multiple chemical species and thus the measured spectra may include the spectral features of multiple chemical compounds. Also, the measured spectra may include the spectral features of the background surface and of the materials in the optical path between the probed surface and the spectrometer, such as water vapor and other vapor-phase chemicals, which can have strong absorption of light at specific wavenumber values. The measured spectra also may include the effects of optical interference and speckle, such as from multiple surfaces in the residue and the underlying substrate as well as from the multiple spatial points of the illuminated spot 16 from which back-scattered light 18 is collected by the spectrometer 10.

FIG. 2 shows a pre-processing 38 for pre-processing the measured spectra, which may include steps such as normalizing the spectral values, mean-centering the spectrum, evaluating derivatives, or differences between the spectral intensities of adjacently measured wavenumber points, and various other linear filtering operations such a peak detection or wavelet transforms. FIG. 2 also shows a background spectrum remover 40 for removing the effect of the background material from the measured spectra of a residue-covered area. FIG. 2 also shows a blind demixer 42 for separating the various spectra from each other spectra associated with the different chemical components in a mixture. The blind demixer 42 may use a Blind Source Separation method, as described by Choi et al. in Blind Source Separation and Independent Component Analysis, Neural Information Processing—Letters and Reviews Vol. 6, No. 1, January 2005, which is incorporated herein by reference. The blind demixer 42 evaluates a set of measured spectra that are obtained by probing multiple different spatial spots 16 of the probed surface 15 in order to measure different mixtures of the spectra. Thus, to obtain these spectra, the controller 30 typically would command the spectrometer to scan the illuminating light 12 over a portion of the probed surface 15, while keeping the set of illumination wavelengths 12 the same. Linear pre-filters in the spectrum pre-processor 38 can be used to increase the sparsity of the input mixtures, which improves the performance of the subsequent blind demixing 42 stage. In some embodiments of the framework, the output of the blind demixer 42 is a set of sample spectra, with each sample spectrum associated with a different demixed or partially demixed component as determined by the blind demixer 42.

Chemical identification for each of the demixed sample spectra is performed by the decision tree guided classifier 44, the non-blind demixer and classifier using sparse representation modeling 46, the region of interest measurements completed decider 47, the confidence weighted Identifier 48 and the known material comparer 49, shown in FIG. 2. The chemical identification makes use of the spectral reference library 20, as discussed later. The non-blind demixing is performed based on the library comparisons and classification of the demixed sample spectrum is performed based on evaluation of a specific sequence of spectral points as guided by the decision tree guided classifier 44.

The spectral library 20 can be organized as a decision tree with decision points at the nodes based on parameters such as the relative intensity value at a particular wavenumber or the curvature (or second derivative) of the relative intensity variation over several adjacent measured wavenumber points, which acts like a spectral peak detector.

Figure 3:
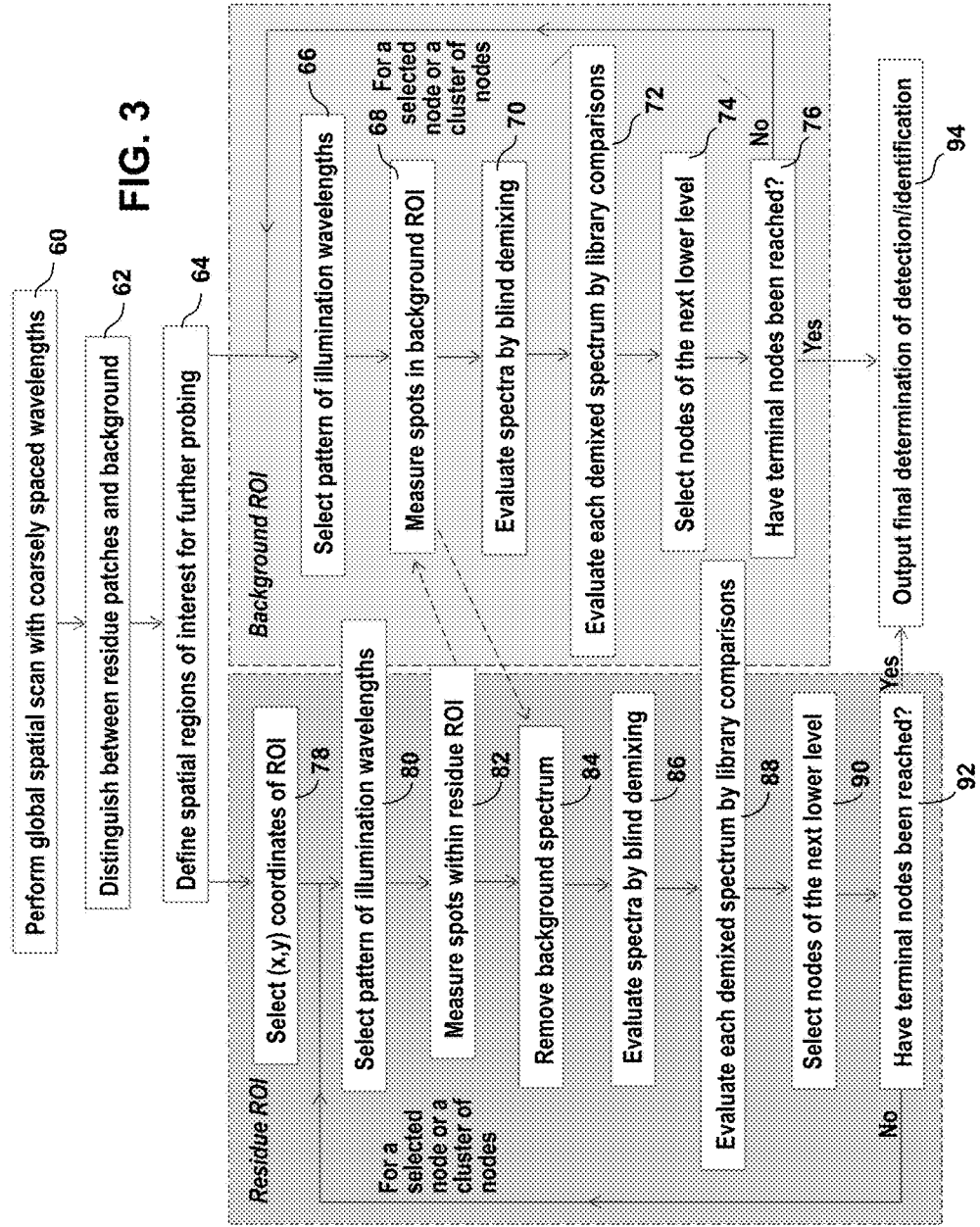
FIG. 3 shows operations performed by the spectrometer-in-the-loop framework in accordance with the present disclosure.

The sensor system framework performs and controls the sensing operations outlined in FIG. 3. These operations can be arranged into 3 groups. The first group, including performing a global spatial scan with coarsely spaced wavelengths 60, distinguishing between residue patches and background 62, and defining spatial regions for further probing 64, shown at the top portion of the FIG. 3, probes the entire area that has been chosen for probing and detection of chemical residues. The first group also separates the overall area into regions that contain residues and regions that are residue free, which are considered the background regions.

The second group of operations, shown at the right portion of the FIG. 3, which include selecting a pattern of illumination wavelengths 66, measuring spots in a background ROI 68, evaluating spectra by blind demixing 70, evaluating each demixed spectrum by library comparisons 72 to perform non-blind demixing and classification, selecting nodes of the next lower level 74, and checking if the terminal nodes have been reached in decider 76, probes selected background regions of interest (ROI) and determines whether there are any chemicals of interest, or target chemical compounds, in the background. In most cases, it is anticipated that the target chemicals will be in the residue-covered regions rather than in the background regions. But it is still often beneficial to determine what chemicals or types of chemicals are in the background, or in the substrate material.

The third group of operations, shown at the left portion of the FIG. 3, which include selecting (x,y) coordinates of a ROI 78, selecting a pattern of illumination wavelengths 80, measuring spots within residue ROIs 82, removing background spectra 84, evaluating spectra by blind demixing 86, evaluating each demixed spectrum by library comparisons 88, selecting nodes of the next lower level 90, and the have terminal nodes been reached decider 92, focuses primarily on the identified residue-covered regions of interest (ROI). However, both spots within the residue covered area and also some residue-free spots nearby may be probed. The measurements of the back-scattering spectra 68 of nearby residue-free spots are used to determine the background spectra associated with the substrate surface so that the substrate contribution to the measured spectra of the residue-covered areas can be removed when performing operation 84. The segmentation of background and ROIs can be done on the basis of spatial uniformity measured using coarse sampling.

Once deciders 76 and 92 determine that the terminal nodes have been reached, a a final determination of detection/identification 94 is outputted.

Multiple spots are measured for each setting of illumination wavelengths. The spectra obtained from these multiple spots are used in the blind demixing operation 86. The blind demixing operation 86 also could be effective for separating out the spectral contribution from the substrate. Thus, the removing the background spectrum operation 84 may sometimes not be performedused.

The spectral reference library 20 can be organized as a branching or clustered structure that contains several levels of nodes, with the nodes of a given level branching into nodes of a lower level until the terminal nodes of the structure are reached. In some embodiments, the evaluation of the demixed sample spectra is done by making comparisons with "prototype" spectra associated with each of the various nodes of the spectral library structure.

The system illustrated in FIG. 2 also can address the cases in which the spectral measurement of a probed area produces a demixed sample spectrum that cannot be matched closely with any of the terminal spectra of the reference library. This "unknown" spectrum as determined by the known material comparer 49 might be associated with a chemical that is not one of the known target or clutter species. Alternatively, this "unknown" spectrum might be associated with a known chemical but for some other state or condition of that chemical in residue form on a surface or in vapor-phase form near a surface. The framework can add this new "unknown" spectrum 100 to the spectral reference library 20 and reorganize the library and decision tree to accommodate the new spectrum.

Figure 4A:
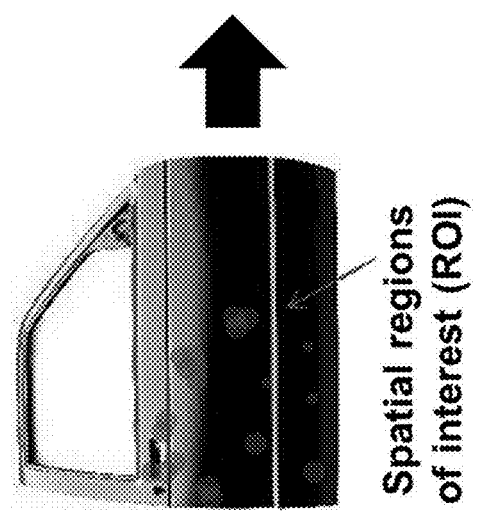
FIGS. 4A and 4B show a residue-covered surface and exemplary spectra of a mixture, as measured, and after demixing with a statistics based algorithm, showing that the spectra of the mixtures in this example appear similar because the clutter is 100× more abundant than the target chemicals in accordance with the present disclosure.

The disclosed sensor system is especially suited for detecting the presence of trace amounts of chemical residues on a surface, such as the surface shown in FIG. 4A. In such cases, the residues generally would cover only a small portion of the overall surface. Also, there may be one or multiple patches of residue-covered surface, with much of the overall surface being residue free. The shapes and sizes of the various residue-covered regions can be quite different from each other. The system can identify the presence of a residue-covered region because its back-scatter spectrum is distinctly different from the back-scatter spectrum of the residue-free areas. The blind demixing algorithm may be used to separate or demix the spectra of the residue-covered region from the spectra of the residue-free areas.

A given residue-covered patch can be defined as a group of spatially adjacent spots that have fairly similar spectral features. In one example, the coordinates of the various spots associated with each patch are stored. Then when a given patch is being probed, those coordinates can be used to control the spectrometer to direct its illumination light onto the spots of that patch. Since the spots are adjacent to each other, the patch can be scanned quite rapidly by relatively small movements of the optical beam-steering hardware of the spectrometer. In an example, the pattern of wavenumbers in the illuminating light is set and the illumination is moved over the multiple spots of a given patch. Also, for this same setting of the wavenumbers, the illumination is then moved to several spots in the residue-free area nearby the patch. This probing of the residue-free area provides a measurement of the spectrum associated with the background or substrate for the residue. As discussed next, the spatial scanning of the spectrometer probe over a given residue can be repeated for several cycles as the chemical detection/identification process progresses, and as guided by results of the library-based classification. The cycles of spectral measurements can be done with progressively higher and finer spectral resolution. For those measurements done at the finer resolution, the wavenumbers of the illumination are sometimes grouped into one or more bands or sub-bands that are spectrally localized.

It is expected, and beneficial, that the measured spectra of the various spots in a patch be somewhat different due to different proportions of chemicals. This difference is exploited to accomplish the demixing. One way to accomplish demixing is to use an independent component analysis (ICA) type algorithm. The ICA algorithm separates a mixture of spectra into the constituent components by optimizing a measure of the statistical independence of the outputs. It relies on the components being statistically independent but does not require prior knowledge of the various spectra of interest, i.e., it operates blindly. An example of a specific ICA algorithm is JADE, which is described by J. F. Cardoso and A. Souloumiac in "Blind beamforming for non-Gaussian signals," IEE Proceedings-F v. 140, n. 6, December 1993, p. 362, which is incorporated herein as though set forth in full.

The ICA algorithm generally requires as inputs a set of measured spectra whose number is equal to or greater than the number of components in the mixture, with the background considered as one of those components. The local spatial scan over multiple illuminated spots in a ROI obtains the multiple input mixture spectra needed for ICA. ICA leverages the variations in concentrations, thickness, surface texture and optical phase interference that occur for different areas of a residue. The small size of the probed spots formed by the spectrometer facilitates the effectiveness of the ICA. Even when the concentration or the signal level due to the clutter or the background is much stronger than the signal level due to the target chemicals in the mixture, ICA can effectively separate out the various spectra associated with those components.

Figure 4B:
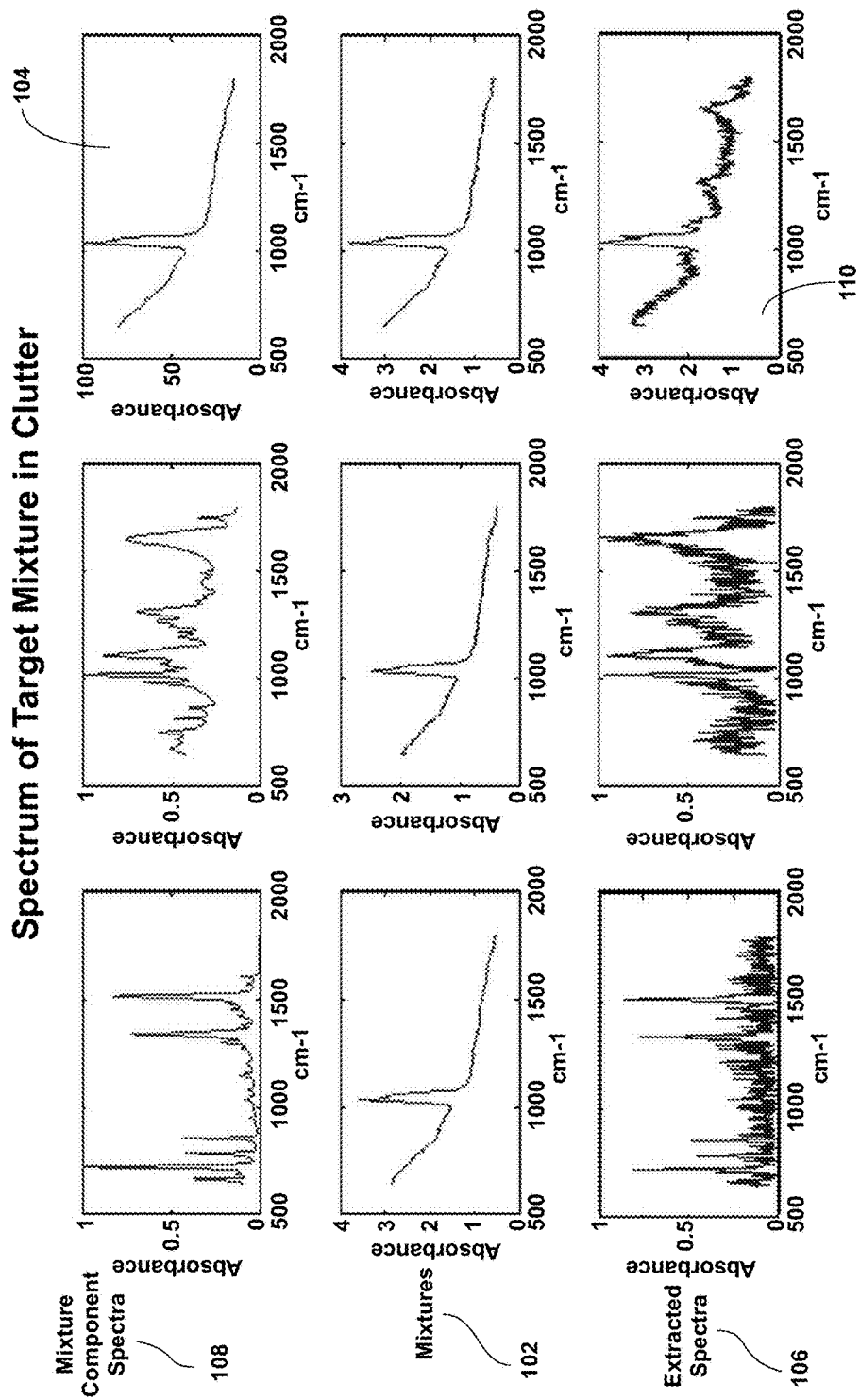

For the example spatial regions of interest (ROI) in FIG. 4A, the mixtures 102 whose spectrums are in shown in the central row of FIG. 4B, contain one component, which is the rightmost spectrum 104, shown in the top row of FIG. 4B, that has 100 times higher concentration than the other two components. Thus, the spectra of the mixture with broadband noise added, 3 examples of which are shown in the middle row 102 of the FIG. 3 all resemble the spectrum of this high-concentration component 104. Nevertheless, ICA is able to demix all three components. The demixed spectra 106 are shown in the lower row 106 of FIG. 4B. It can be seen that the demixed spectra are quite similar to the spectra of the original un-mixed chemicals, shown in the upper row 108 of FIG. 4B, and all the key spectral features are recovered. The main difference is that the demixed spectra 106 generated by ICA of the low-concentration components have substantial noise, since noise was added to make the net signal-to-noise ratio of the mixture data 20 dB. Also, the demixed spectrum 110 corresponding to the high-concentration clutter component 104 has additional weak features that were not part of the original spectrum of that component. These additional features are from the other components in the mixture, but are not strong enough to affect recognition accuracy.

Figure 5:
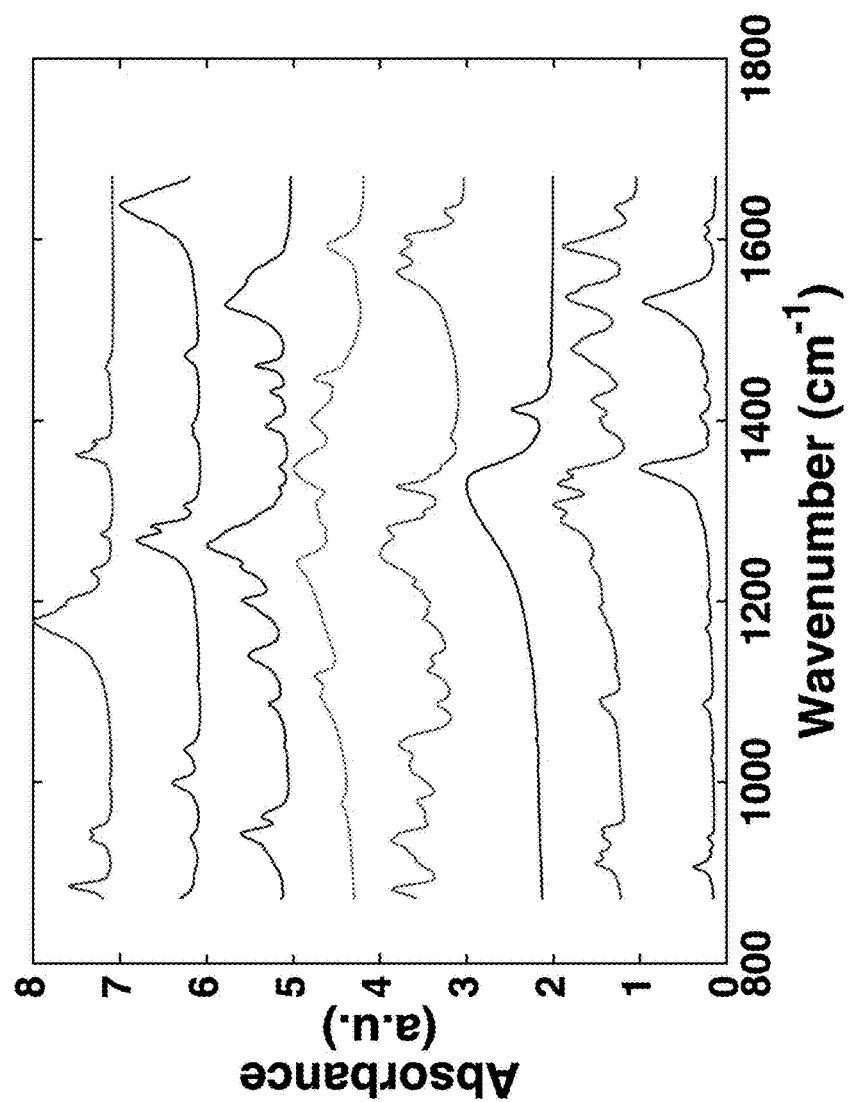
FIG. 5 shows infrared absorption spectra associated with several exemplary chemicals in accordance with the present disclosure.

To better understand the rationale behind the choices of the illumination wavenumbers, examples are shown in FIG. 5 of several characteristic absorbance spectra that are associated with specific chemical compounds. These spectra are plotted with different offsets in the vertical axis so that their features can be clearly distinguished. Especially interesting is the wavenumbers at which the spectral features occur.

FIG. 5 shows exemplary spectra for 8 different materials (A, B, C, D, E, F, G and H). Each of these absorbance spectra contains peaked features that are located at specific wavenumbers. The shape and spectral location of the features are indicative of the material, since they are associated with the energy of vibrational transitions for those molecules. As a point of reference, the gray bands, such as gray bands 3, 4 and 5, shown in FIG. 5 have a width of approximately 10 $cm^{-1}$. We assume that the wavenumber of the illumination coincides with the center of a gray band shown in the FIG. 5.

For some materials, such as A, the spectrum has a distinct peak (labeled 1) that is located at a wavenumber for which the spectra of the other materials do not have any strong feature. For other materials, such as B, it is the absence of spectral features at the wavenumbers for which other materials have spectral features that is the distinguishing factor. The spectrum for material B has a broad and structured peak at the wavenumber of the band labeled 2. Other materials (such as C, E, F and G) also have peaks at this wavenumber. But these other materials have additional spectral peaks at other wavenumber values (between 1000 and 1600 $cm^{-1}$, for example) whereas material B does not.

The gray bands labeled 3, 4 and 5 illustrate how illumination at 3 different selected wavenumbers can be used to distinguish between materials C, D, E, G and H. The spectral peaks for each material coincide with a unique combination of the 3 wavenumbers. For example, the wavenumber bands at which a peak occurs are: material C (3, 4), material D (5 only), material E (4, 5), material G (3, 5), and material H (3 only). This spectral discrimination capability is achieved because some of the spectral peaks are sufficiently narrow and/or sufficiently well separated to be distinguishable at the spectral resolution (of 10 $cm^{-1}$ in this example) of the measurement, as illustrated by the peaks labeled 6. The set of bars and spaces between bars labeled 7 in FIG. 5 illustrate the limitation of insufficient spectral resolution. The bars highlighted have a width of 10 $cm^{-1}$ and are spaced 10 $cm^{-1}$ apart. At this spectral resolution of 10 $cm^{-1}$, it would be difficult to reliably distinguish the narrow peak in the spectrum of material E and the fine features in the spectrum of material G, but the coarser features in the spectra of the other materials should be clearly distinguishable. Finally, the gray bands labeled 8 in FIG. 5 correspond to another group of spectral features that occur in the spectra of several materials and that can be used to confirm an initial identification decision. A decision on the detection/identification of a chemical material might be done with greater confidence if the laser source in the spectrometer has sufficiently large spectral coverage to also provide light at these wavenumbers of the additional group of spectral features.

FIG. 6 illustrates how a combination of an initial "blind" spectral measurement at coarse wavenumber resolution followed by one or more adaptively guided spectral measurements at finer wavenumber resolution may be used to distinguish between and identify the components in a mixture of chemicals that are in the same residue patch. A mixture of 3 components is considered in this example, with each component having the same relative concentration. The spectra associated with each of the 3 components are shown as solid curves, of red, blue or violet color. The spectrum obtained for the mixture is shown as the black dashed curve.

Figure 6A:
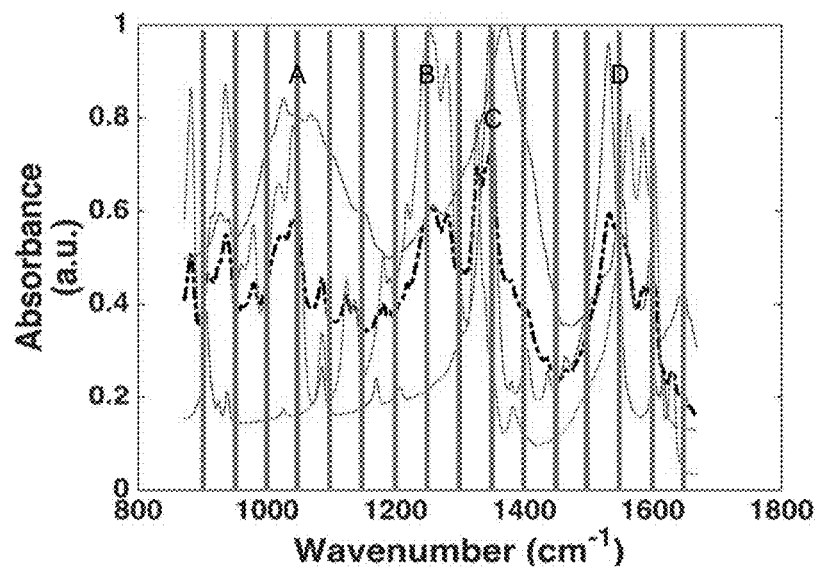
FIGS. 6A and 6B show an infrared absorption spectra of a mixture comprising three exemplary chemicals, FIG. 6A probed with coarsely spaced wavenumbers, and FIG. 6B probed again with groups of more finely spaced wavenumbers with the spectra of the component chemicals shown in the solid red, blue and violet curves, and the spectrum of the mixture shown in the black dashed curve in accordance with the present disclosure.

FIG. 6A shows how light comprising a set of uniformly spaced wavenumbers, which are indicated in FIG. 6 by the pink vertical stripes, covering the entire spectral span can be used to probe the residue ROI and determine spectral regions or bands of interest (BOI) at which relevant chemical-signature features might be present. As illustrated in FIG. 6A, light at the 4 wavenumber values labelled A, B, C and D experience stronger absorption than light at the other wavenumbers probed.

Figure 6B:
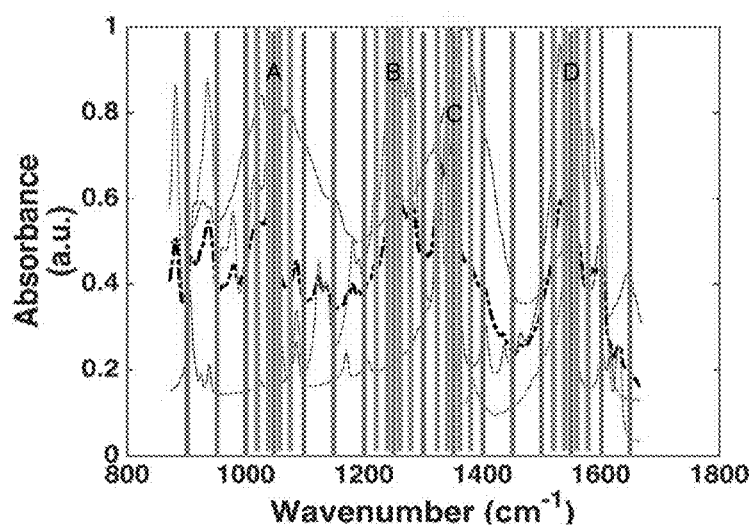

FIG. 6B shows how multi-wavenumber light at a finer wavenumber spacing, as indicated by the vertical green stripes, can be used for additionally probing each of the four BOI in the vicinity of wavenumbers A, B, C and D. The width of each green stripe is approximately 10 $cm^{-1}$ and the spacing between adjacent green stripes also is approximately 10 $cm^{-1}$. Probing at the BOI around wavenumbers A and C would enable discrimination between the three chemical components. For example, the violet chemical has a broad absorption peak in BOI A and the red chemical has a narrow double-peak in that BOI whereas the blue chemical has very little absorption in that BOI. For BOI C, the relatively narrow absorption peaks for the blue and red chemicals are located at different wavenumber values and the absorption peak for the violet chemical is broader in comparison. Additional spectral measurements at the other two BOI, B and D, will provide even more discrimination between the components in the mixture when considered together with the measurements from BOI A and C.

The combination of measured back-scatter spectral data at both the coarse wavenumber spacing (e.g., 50 $cm^{-1}$) and also the finer wavenumber spacing (e.g., 10 $cm^{-1}$) is provided by the framework to the ICA algorithm for demixing. The goal of this demixing is to obtain the demixed spectra (red, blue and violet curves) at those wavenumber values that were measured by the spectrometer. Note that since the results from the initial measurement at the coarse wavenumber spacing are used to define the BOI and also the wavenumber values for the subsequent measurements at the finer wavenumber spacing, the total number of wavenumber points that must be measured is greatly reduced. Care should be taken, however, to not reduce the number of wavenumber points below that required by ICA. Those wavenumber points most salient to the demixing of the red, blue and violet chemicals in the mixture and to the identification of those chemicals (to be discussed later) are the ones selected by the framework for illuminating that particular residue ROI.

Figures 7A, 7B:
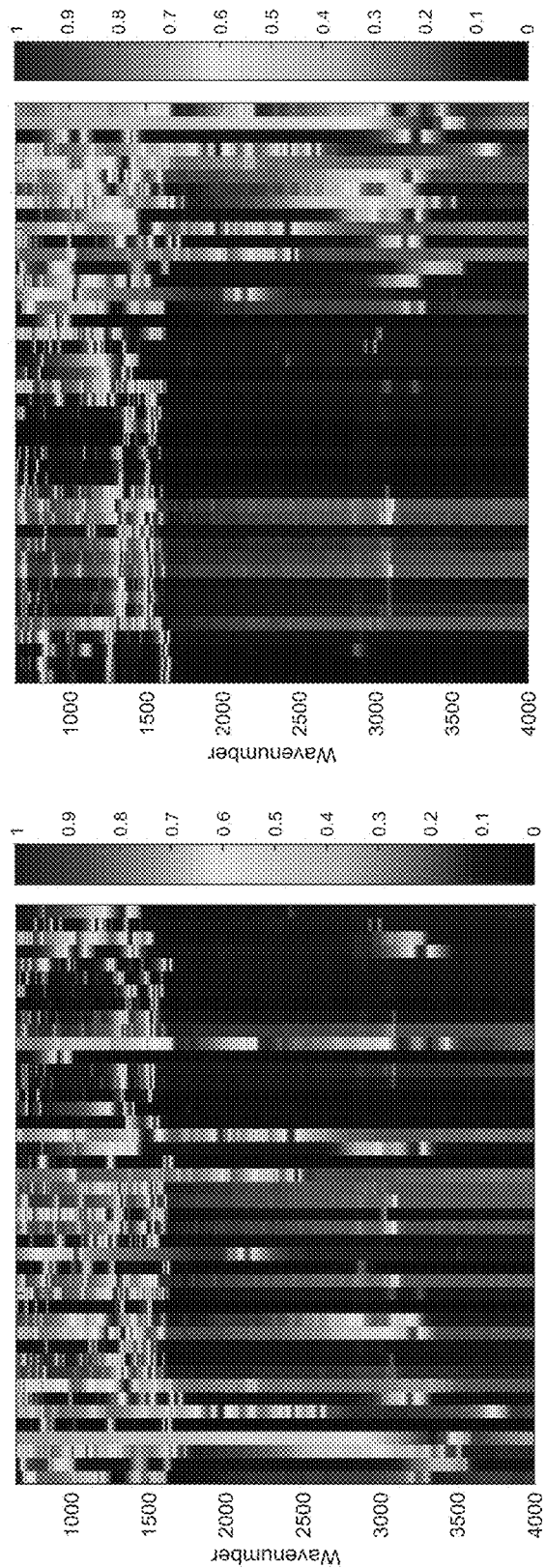
FIGS. 7A and 7B show examples of reference spectra in a structured spectral-reference library, showing in FIG. 7A the various spectra as originally presented and in FIG. 7B those same spectra organized into clusters based on their similarity in accordance with the present disclosure.
Figure 8:
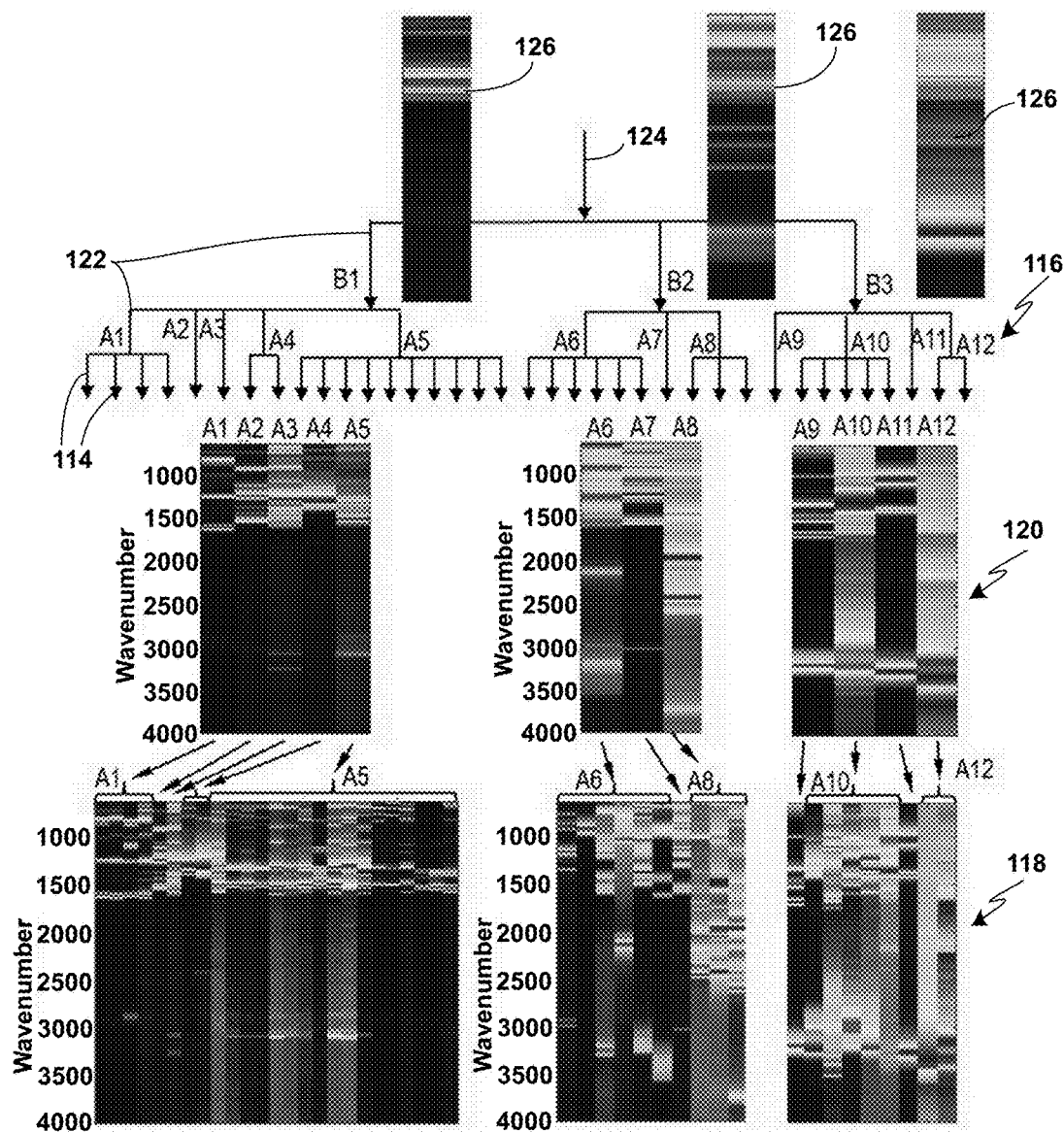
FIG. 8 shows an example of a structured spectral-reference library including the reference spectra of FIGS. 7A and 7B, showing the tree-clustered hierarchical structure and spectra associated with the intermediate nodes and terminal nodes of the structure in accordance with the present disclosure.

An example of a structured library of reference explosives spectra is illustrated in FIGS. 7A, 7B and 8. FIG. 7A shows the various reference spectra as they were initially provided and FIG. 7B shows those reference spectra after they were grouped into clusters. Each spectrum is shown as a column with the wavenumber of the light indicated along the vertical axis of the plot and the relative absorption at a given wavenumber indicated by the color at that position in the column. The highest intensity is red and the lowest intensity is blue. Sharp spectral features appear as abrupt and narrow colored bands and broad spectral features appear as broad and gradual changes in the color. The grouped organization of the reference spectra is evident in FIG. 7B from the horizontal bands of color that extend over multiple columns. This is indicative that those chemicals of the same group or cluster have spectral features occurring at the same or close wavenumbers. This spectral similarity suggests those chemicals have similar bond types. For example, those chemicals may all contain amino groups or those chemicals may all contain aromatic components.

Various rules can be used to organize the reference spectra into defined clusters. Also, these rules can be used to organize multiple clusters into higher-level clusters. These rules evaluate and compare the spectra of the lower-level nodes. For example, the clusters shown in FIG. 7B were defined by first constructing an N-dimensional vector associated with each spectrum for which each of the N dimensions is a different wavenumber value at which the spectrum was measured. The length of the vector in each of the N dimensions is the value of the spectral intensity at that associated wavenumber. A rule such as one that minimizes the Euclidean distance between the N-dimensional vectors for two spectra is then used to evaluate the similarity of those two spectra. Note that different rules could be used to define the clustering for different levels of the overall library structure. Also, other measures besides Euclidean distance could be used to define a cluster.

An example of a hierarchical organization of a library of reference spectra shown in FIG. 7A is depicted in FIG. 8. A set of initial reference spectra is organized as the leaves 114 of a tree-like hierarchical structure 116 that has multiple levels of nodes. The reference spectra 118 are associated with the terminal, lowest-level nodes 114 of the hierarchical structure 116. Those terminal nodes 114 are grouped into clusters that are then further grouped in larger clusters. Each cluster resembles a branching sub-structure and is associated with an intermediate node 122. Multiple intermediate nodes 122, and their constituent nodes, are then grouped into larger clusters, with each larger cluster associated with an intermediate node 122 at a next higher level of the hierarchically structured library that may be stored in memory 20. The hierarchical structure 116 shown in FIG. 8 has a lowest level of terminal nodes 114, 2 levels of intermediate nodes 122 and a starting or top node 124. The highest intermediate level 122 (level B) has three clusters. Cluster B1 comprises mainly materials whose spectra have content primarily in the wavenumber range between 800 and 1700 $cm^{-1}$ and have one or more strong spectral features in the wavenumber range between 1200 and 1700 $cm^{-1}$. Cluster B3 comprises materials that also have significant spectral features in the wavenumber range between 2700 and 3600 $cm^{-1}$. Cluster B2 comprises the rest of the material in the library and their spectral features are located over a large spread of wavenumbers. These similarities are clearly evident from the groups of terminal-node spectra 118 shown in FIG. 8. The distinction between the spectra in a cluster is evident from comparing the prototype spectra 126 for the three nodes B1, B2 and B3.

FIG. 8 also shows the organization of the three main clusters into sub-clusters, with those sub-cluster nodes located at level A in FIG. 8. Cluster B1 has 5 sub-clusters, A1 through A5. Cluster B2 has 3 sub-clusters, A6 through A8. Cluster B3 has 4 sub-clusters, A9 through A12. Some sub-clusters, such as A5, have many terminal-node spectra 114, in this case 10 spectra. Other sub-clusters (such as A2, A3, A7, A9, and A11) have only a single terminal-node spectrum. One can clearly see from these examples that the reference spectra that are part of the same sub-cluster generally have spectral features that are located at approximately the same wavenumbers. They also have similar kinds of spectral features, for example sharp features compared to broad features. This kind of library structure facilitates the classification of a measured spectrum according to the match between that measured spectrum and the reference spectra of the library because it highlights the similarities and differences between those spectra. The prototype spectra 120 for the nodes A1 through A12 that connect to sub-clusters A1 through A12, respectively, also are shown in FIG. 8.

Prototype spectra associated with the intermediate nodes 122 of a hierarchical structure 116 can be constructed using various methods. For example, the prototype spectra 120 and 126 shown in FIG. 8 are linear combinations of the spectra in their underlying nodes, with those spectra having equal weights. Each prototype spectrum is obtained by summing together the intensities of those underlying spectra at the same wavenumber point, point by point. Each prototype spectrum is then normalized so that its peak has a value of 1. The intensity scale for the spectra shown in FIG. 8 is linear.

Other ways of organizing a spectral library can be employed that facilitate the efficient detection and identification of a chemical using the wavenumber values of the features in its spectrum, rather than enhance the spectral differences or similarities between the reference spectra as done by the library structure 116 of FIG. 8. For example, to define the highest intermediate level, the various reference spectra may be grouped according to the wavenumber value of their strongest spectral feature. The next highest intermediate level has its clusters defined by considering the second strongest spectral feature in the reference spectra. The following intermediate level has its clusters defined by considering the third strongest spectral feature, and so on. For this example, if a given reference spectrum has more than one dominant spectral feature, with those dominant spectral features having approximately the same strength, that reference spectrum can be assigned to multiple clusters and thus multiple terminal nodes of this library structure.

In yet another example of the organization of a structured spectral-reference library 20, only those spectral peaks that are stronger than a given normalized value (such as 0.3) are considered in the structuring of the nodes. The wavenumber of the broadest spectral peak is considered when defining the clusters of the highest level of the structure. Then the wavenumber of the next broadest spectral peak is considered to define the sub-clusters of the next highest level. This process is continued until all of the reference spectra are assigned a level of the hierarchical library structure 20 for which each terminal-node spectrum is clearly distinguishable from the other terminal-node spectra of that sub-cluster because the spectral peaks being considered for that sub-cluster's evaluations are located at different wavenumber values. With this organization, one can start at the top of the library structure and then progress level-by-level down into the clusters and sub-clusters by observing the presence or absence of a spectral peak at some wavenumber value. The spectral resolution needed for those observations becomes progressive finer as one continues to progress lower into the hierarchical structure.

Another way to organize the reference spectra is in the form of a decision tree, with those reference spectra associated with the terminal nodes or leaves 114 of the decision tree. Typically, the set of reference spectra as well as variations of those reference spectra are used to train the decision tree. Variations could be obtained by adding noise to the reference spectra or by adding other forms of distortion (such as spreading and shifting of spectral peaks) to the reference spectra in order to increase robustness.

Figures 9A, 9B:
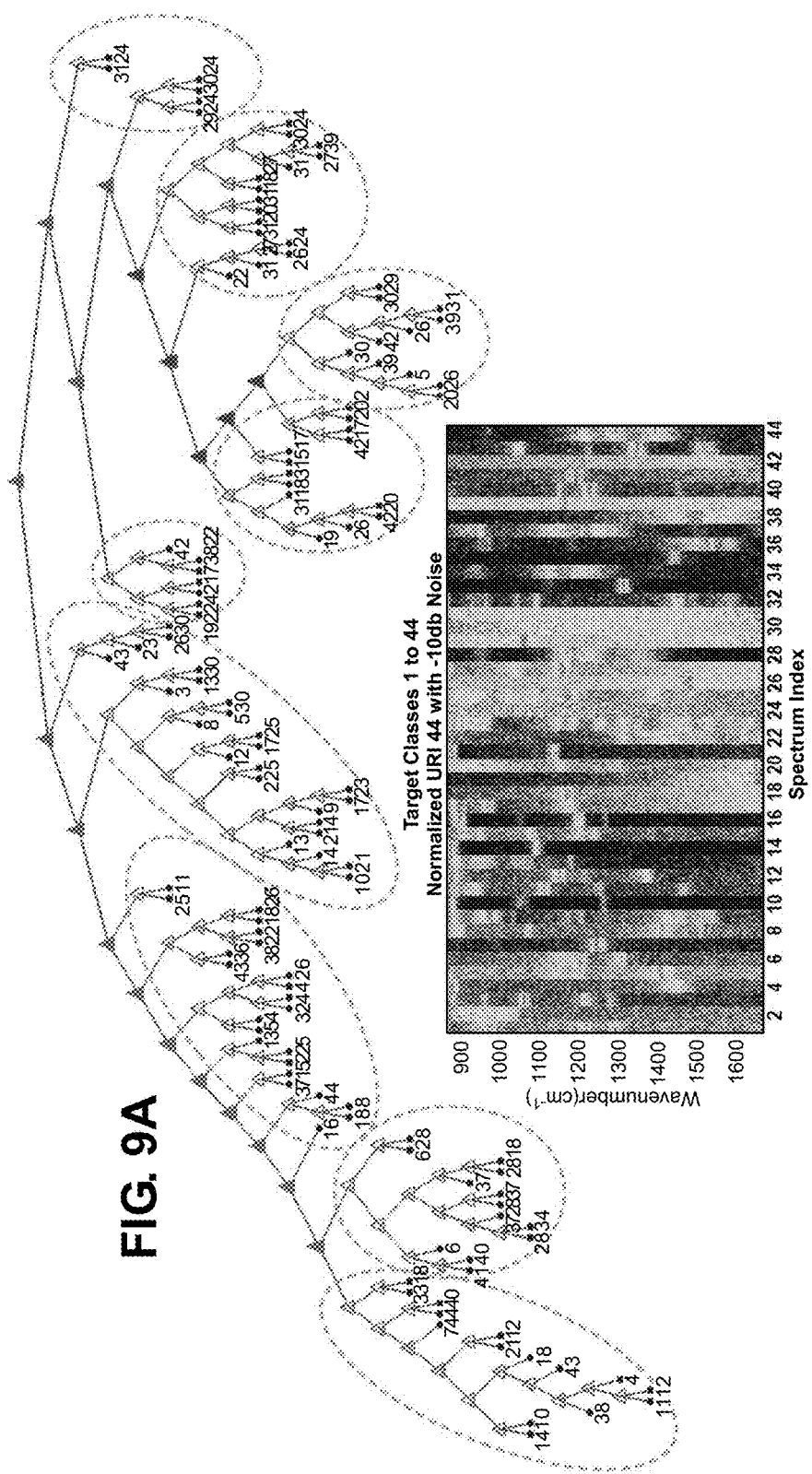
FIG. 9A shows a decision tree constructed to distinguish between 44 different reference spectra shown in FIG. 9B, by using multiple copies of those 44 spectra with noise added to train the decision tree in accordance with the present disclosure.

FIG. 9A shows a decision tree that was constructed by training with the 44 spectra shown in FIG. 7A but only the portion of those spectra between 870 and 1670 $cm^{-1}$ was included, as shown in FIG. 9B. A decision tree comprises a set of decision nodes arranged in a tree-branching structure. Each path through a series of decision nodes and branches ends at a terminal node that is associated with a particular reference spectrum (as indicated by the spectrum-index number of that spectrum). Every reference spectrum is associated with at least one terminal node of the decision tree. As illustrated in FIG. 9A, a given reference spectrum can be associated with multiple terminal nodes 114, or leaves, of the decision tree. For the exemplary decision tree shown in FIG. 9A, the intensity at a given wavenumber is compared with a threshold value at each node of the tree. If the intensity is greater than or equal to the threshold value, the right branch of the tree is followed and if the intensity is less than the threshold value, the left branch is followed. Different wavenumber points are considered at different nodes of the tree, although a given wavenumber point may be considered at several nodes in some decision trees, such as the one illustrated in FIGS. 11A, 11B and 11C. Decision trees can be learned from data using methods such as the C5 algorithm, as described by J. R. Quinlan in tutorials and references available at URL: http://www.rulequest.com), which are incorporated herein as though set forth in full.

Other decision trees can be constructed from the same set of reference spectra by using other rules for the decision nodes. For example, instead of considering the intensity of the back-scatter signal at a given wavenumber point, the decision node could consider the local curvature (or second derivative) of the spectrum associated with that wavenumber point and its surrounding wavenumber points. Decisions based on curvature may be more useful for detecting the peaks and dips that are associated with the reflection or absorption of light associated with molecular resonances.

A combination of decision trees or a decision tree that considers several types of rules also could be used. For example, with the coarsely spaced and relatively evenly spaced wavenumber points that may be measured in an initial measurement of a residue patch, it may be more suitable for the higher-level decision points to use a rule that looks for wavenumber points of high intensity. Evaluation of curvature requires illuminating the residue patch with several wavenumbers that are relatively close to each other. Thus, curvature may be more suitable for later or lower-level decision points that can have available several measurements at closely spaced wavenumbers.

The nodes of a decision tree can be grouped into clusters. Examples of clusters are highlighted by the dashed boundaries shown in the decision tree depicted in FIG. 9A. Clusters of higher-level nodes in the decision tree are indicated by the colored triangles. Each cluster of nodes also represents a group of wavenumbers, or of wavenumber sets in the case of curvature decisions, that could be illuminated to probe the ROI. Clustering of the decision nodes provides a way to reduce the number of wavenumber points that must be measured when probing a given ROI to determine its chemical content. Some of the clusters include only lower-level nodes and other clusters include only higher-level nodes. In general, since only a few chemicals typically are present in a given ROI being probed, only a few clusters of the tree structure would need to be considered and other clusters can be ignored.

The process of associating a particular chemical or end-member spectrum with the measured spectra obtained at a given spatial region of interest and thus of identifying the chemicals constituting the residue at that spatial location involves progressing through the tree structure of the library from top to bottom and following selected branches into clusters and sub-clusters until one or more terminal nodes or lowest-level sub-clusters are reached. At each node of the tree, the system controller 30 controls the sensor 10 to first measure the spectra at the selected set of wavenumbers of multiple spots in a residue region of interest. The sensor system also may measure nearby spots that are residue free. These various measurements are pre-processed and also may have effects of the background spectrum removed, as described above with reference to FIG. 3. The measured spectra are then processed using a blind demixing algorithm such as ICA to construct one or more demixed spectral samples. Each of these sample spectra is then processed by the classifier 44, which may use a sparse representation-based classification (SRC) algorithm, that compares the sample spectrum with a weighted combination of library spectra.

ICA and SRC classification of spectra are described in U.S. patent application Ser. No. 15/280,575, filed Sep. 29, 2016, and in U.S. patent application Ser. No. 15/283,358, filed Oct. 1, 2016, which are incorporated herein as though set forth in full. Such an approach is more effective if the blind demixing produces a sample spectrum whose constituents, if not completely demixed, are in the same cluster or sub-cluster of the tree structure, and thus are in the nodes below the node being evaluated. Use of a SRC approach in those cases for which one of the constituents in the sample spectrum is not part of the cluster (or sub-cluster) can lead to an erroneous classification or to the inability to make any classification since the SRC considers only those reference spectra that are in the given cluster. Thus, it is important to select the wavenumber points of a spectrum measurement to facilitate the blind demixing, especially in the early steps of a chemical identification process (i.e., for the higher level nodes of a tree-structured library organization).

The different kinds of library organizations discussed above can provide different ways to specify and control the wavenumber values of the multi-wavelength light that illuminates a spot being probed. For example, the wavelengths in the beams of illumination light can be controlled to change from one measurement instance to the next while the spectrometer remains pointed at a given spot or in a given ROI. In some embodiments, the hierarchically structured reference library and the prototype spectra of the intermediate nodes in that library structure can be used to determine the wavelengths or wavenumbers of the illumination light.

As an example, consider the spectra shown in FIG. 8. Starting at the top of the tree structure, one can determine whether to explore cluster B1, cluster B2 or cluster B3 by first probing a residue region with a set of uniformly spaced wavenumber values. If the chemicals in the residue are associated with cluster B1, the measured spectrum should have its main spectral features in the wavenumber range between 1200 and 1600 $cm^{-1}$. And, if the chemicals in the residue are associated with cluster B2, the measured spectrum should have some of its main spectral features in the wavenumber ranges outside 1200-1600 $cm^{-1}$. Likewise, if the residue contains chemicals associated with cluster B3, the measured spectrum should have significant spectral features in the wavenumber range of 2700-3600 $cm^{-1}$. Determination of the cluster B1, B2 or B3 that best matches the measured spectrum can be used to guide the selection of the wavenumbers of the light used in subsequent probing of the residue. Thus, if the initial measurements indicate the chemical is in cluster B1, most of the wavelengths selected in a subsequent measurement will be in the wavenumber range between 1200 and 1600 $cm^{-1}$ and can be selected to provide discrimination between sub-clusters A1 through A5, for example.

As an example, the prototype spectra 126 associated with the intermediate nodes B1, B2 and B3 of the structure 116 in FIG. 8 can be used as reference spectra by the ICA/SRC algorithms that process the spectral measurement results obtained from a first probing of a residue region with a set of uniformly spaced wavenumber values. These algorithms can determine whether each demixed spectrum generated by ICA from the initial spectral measurements is matched more closely by the prototype spectrum for node B1, B2 or B3. Depending on whether the sub-cluster associated with node B1, B2 or B3 is selected by this matching process, the system controller 30 can the select a second set of wavenumber values to use for probing that residue region. For example, if sub-cluster B2 is selected, the second set of wavenumber values would be chosen to distinguish between the prototype spectra 120 associated with nodes A6, A7 and A8.

Figure 10A:
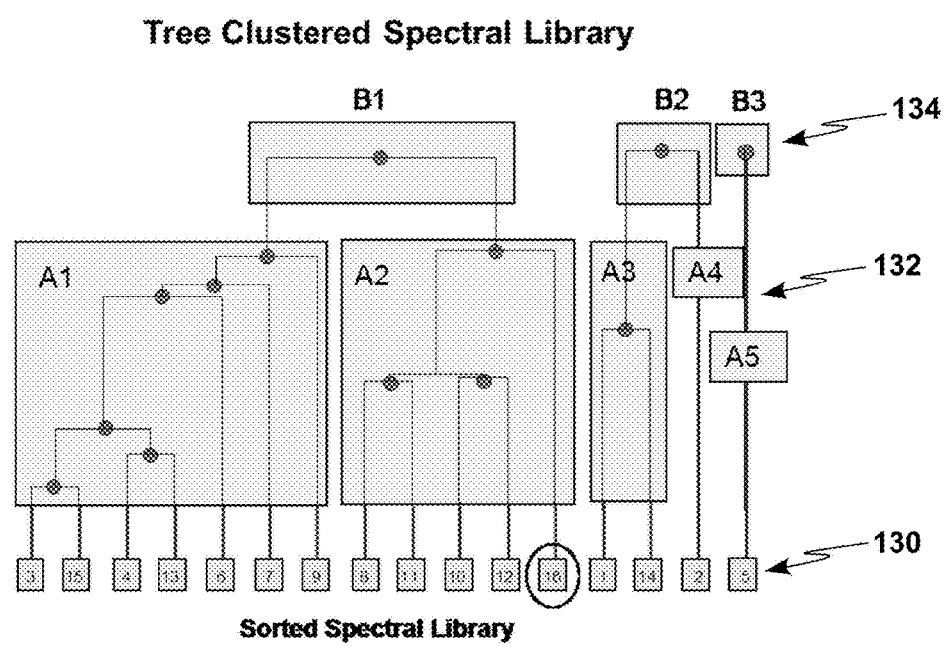
FIGS. 10A and 10B show examples of a structured spectral-reference library, showing in FIG. 10A a tree-clustered hierarchical structure and in FIG. 10B spectra associated with the various nodes of the structure in accordance with the present disclosure.
Figure 10B:
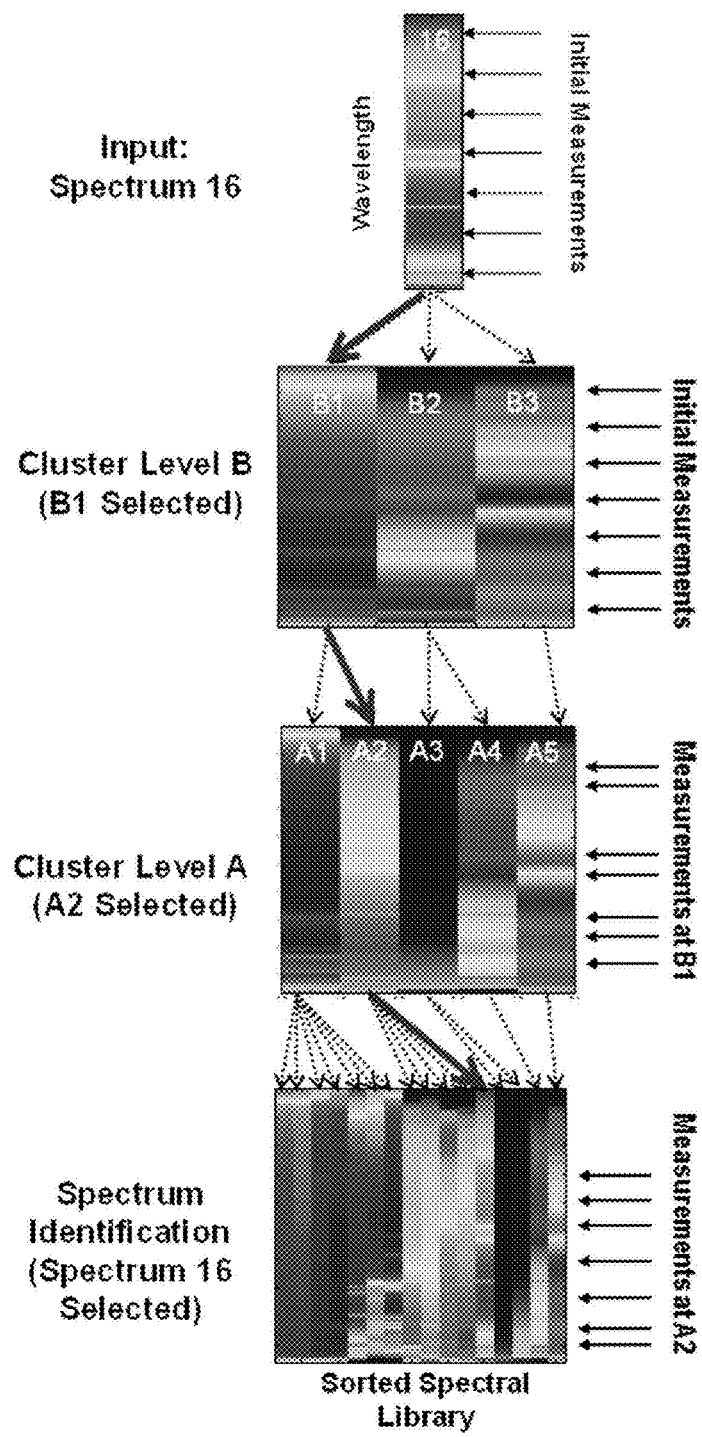

FIGS. 10A and 10B illustrate another, simpler, example of a structured library of reference spectra organized according to the similarity of those spectra. This structure contains a level of terminal nodes 130 and two levels of intermediate nodes—level A 132 and level B 134. For the exemplary structure of FIG. 10A, one level of intermediate nodes 132 includes nodes A1, A2, through A5. A next higher level of intermediate nodes 134 includes nodes B1, B2 and B3. Each higher-level node represents a cluster with branches into a set of next-lower level nodes. For example, node B1 branches into nodes A1 and A2. In the structure of FIG. 10A, some higher-level nodes have only a single lower-level node associated with it. For example, node B3 is connected only to node A5, which is connected only to one of the terminal nodes 130, namely terminal node 5. A prototype spectrum is associated with each intermediate node. This prototype spectrum is a composite of the spectra associated with the underlying nodes of that cluster. Examples of the prototype spectra are shown in FIG. 10B. The reference spectra associated with the 16 terminal nodes also are shown in FIG. 10B.

FIG. 10B also illustrates how a sequence of spectral measurements at selected combinations of wavenumbers can be commanded by the framework to determine or identify the chemical component in a residue. For this example, we assume that the blind demixing algorithm, such as ICA, which may be implemented after each spectral measurement can adequately separate the spectrum of that component from spectra of any other components in a mixture of which that component is a part.

For a more specific example, we assume the residue comprises a chemical whose back-scatter matches that of reference spectrum 16 of FIG. 10A. The spectrum of the exemplary chemical component in the residue is shown at the top of FIG. 10B. However, that spectrum is observed or measured only at those wavenumber points indicated by the arrows at the right of FIG. 10B. In this example, the wavenumber points of the initial measurement are selected to have a uniform, coarse spacing that covers the entire spectral span. The system controller provides the data from this initial spectral measurement to the blind demixer 42 and then provides the demixed spectrum sample generated by the blind demixer 42 to the library-comparing classifier 44 together with the classifier 46 with the prototype spectra for B1, B2 and B3 being the potential target spectra whose linear combination is matched with the demixed spectrum sample, assuming the SRC algorithm is used by the classifier 46. The classification algorithm determines that the pattern of the back-scattered light for these initial probe wavenumbers best matches the prototype spectrum for cluster B1. Since cluster B1 includes sub-clusters A1 and A2, the set of additional wavenumbers for the next measurement is selected because the prototype spectra for A1 and A2 are the most dis-similar at those wavenumbers. The combination of data from both this next spectral measurement and the previous initial spectral measurement is then directed by the controller to the blind demixer 42, whose demixed sample spectrum is directed by the controller 30 to the non-blind classification algorithm, such as SRC. The classification algorithm determines, for example, that the best match is with the prototype spectrum for sub-cluster A2. For the following spectral measurement, the set of additional wavenumbers at which the reference spectra 8, 10, 11, 12 and 16 are most dissimilar is selected. After this third spectral measurement, the residue will have been probed with 3 sets of wavenumbers and the combination of back-scattered intensity values measured at these 3 sets of wavenumbers defines a net measured spectrum that can be used to identify the chemical. The data from these 3 spectral measurements is again directed to the blind demixer 42 and the new sample spectrum output from the blind demixer 42 is directed, by the controller, to the classifier 46 for the identification of the chemical in the residue according to the match between its measured spectrum at the wavenumbers selected by the controller 30 and the reference spectra in the sub-cluster A2.

The simple example discussed above illustrates the use of the library spectra to select the wavenumbers of the illumination light for subsequent measurements. However, it is clear from this example that the method relies on the combination of the blind demixer 42 and the classifiers 44 and 46, for example using SRC to sufficiently demix the measured spectral data so that each demixed component can be assigned to only one cluster and sub-cluster. For some mixtures of the chemicals in a residue, the data obtained at the measured wavenumber points may not be sufficient to enable a sufficiently complete demixing (e.g., by ICA) and the sample spectrum still comprises multiple compounds. In some cases, the classification (e.g., SRC) may indicate that the sample spectrum comprises multiple compounds that are in different clusters of the hierarchical library. If these compounds are part of several different clusters of the hierarchical library (e.g., both cluster B1 and cluster B2), two or more sets of additional spectral measurements would be needed, with one measurement using wavenumbers selected for the first cluster (e.g., cluster B1) and a second measurement, at that same level of the tree structure, using wavenumbers selected for the second cluster (e.g. cluster B2). It is important that the combination of the blind demixer algorithm 42 and the non-blind classification algorithm 46 (e.g., the combination of ICA and SRC) determine whether the subsequent spectral measurements should include the wavenumber points in only one cluster or in multiple clusters branching from a given node. This is because after a cluster assignment has been made, future spectral measurements do not consider the spectral features of the chemicals in other clusters that were not assigned.

In some cases, it may be beneficial to pre-process the reference spectra (or terminal-node spectra) and the prototype intermediate-node spectra derived from them in order to emphasize certain kinds of spectral feature and de-emphasize other spectral features. For example, the intensity scale for the spectra shown in FIG. 8 is linear. Alternatively, a logarithmic or exponential transformation (i.e., a change in the intensity scale) could be used to emphasize the presence of spectral peaks. Also, a first and/or second derivative of the spectral data could be calculated to distinguish between sharp or abrupt spectral features and broad spectral features. Thus, the spectrum pre-processing could be applied both to the measured spectral data obtained from a region being probed and also to the reference spectra and the prototype intermediate-node spectra. The specific pre-processing methods used at a given time could be selected based on knowledge about the background conditions of the probed surface and also about the measurement conditions (such as the angle-of-incidence of the probe light with respect to the probed surface). In some embodiments, various pre-processed reference spectra derived from the same original reference spectrum could be stored in the spectral library 20. In other embodiments, the pre-processing of a specific reference spectrum could be done by the classifier 46 or the library-comparison by classifier 44, as needed.

Figure 11A:
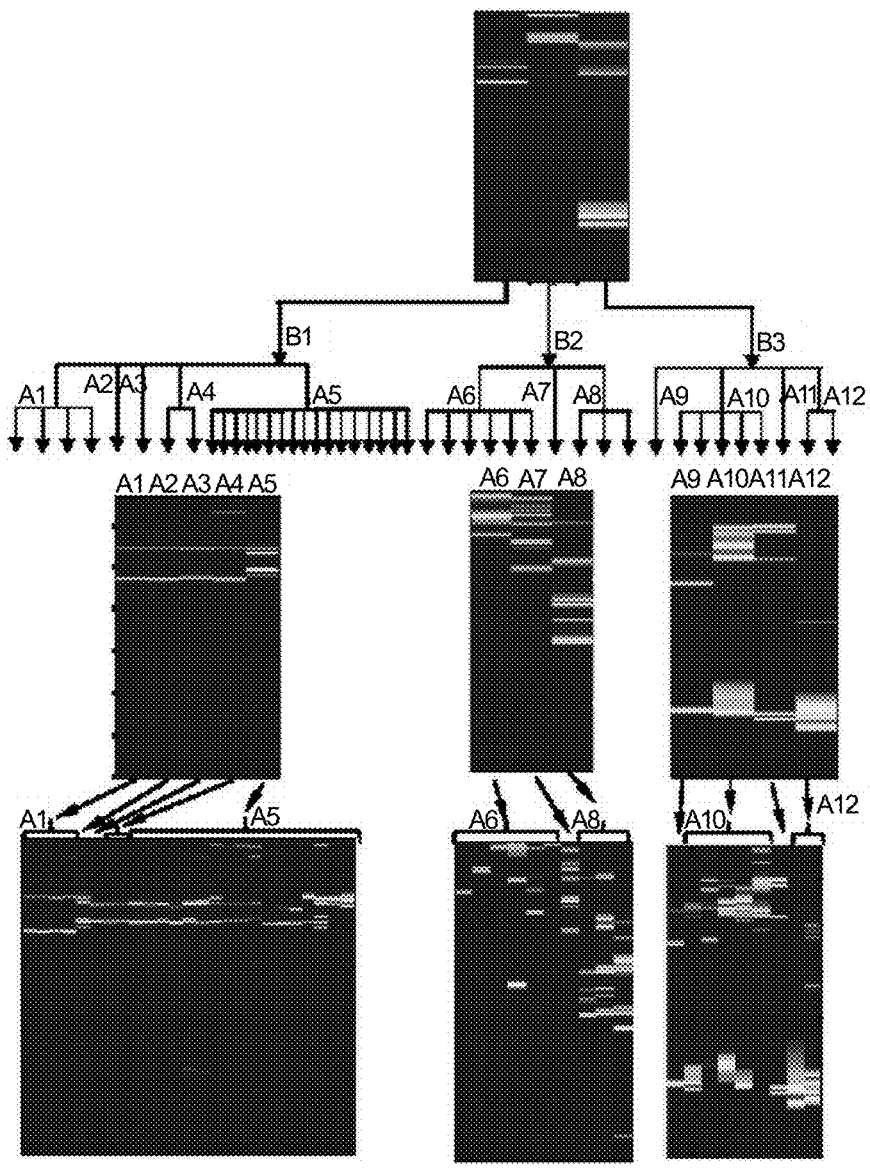
FIGS. 11A, 11B and 11C show examples of the structured spectral-reference library of FIG. 8 after its spectra have undergone pre-processing operations.
Figure 11B:
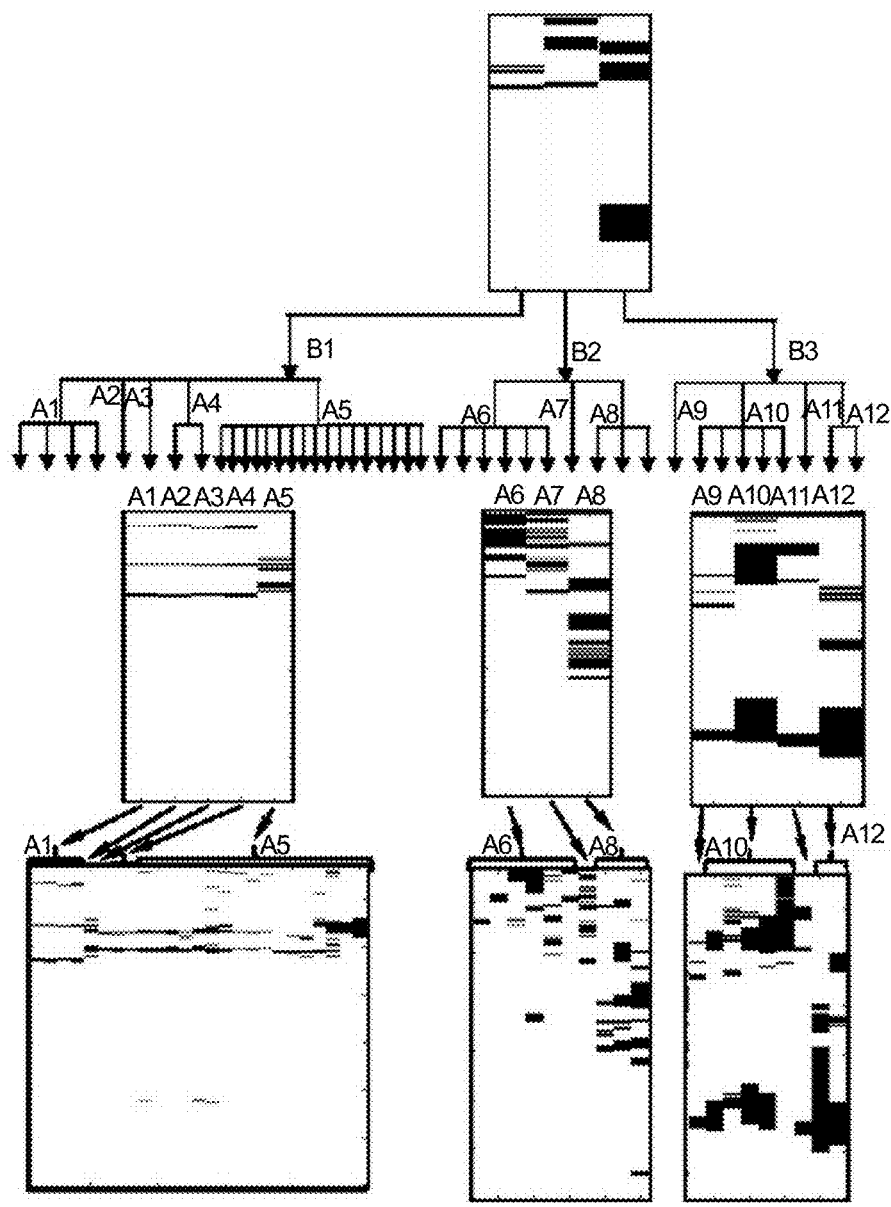
Figure 11C:
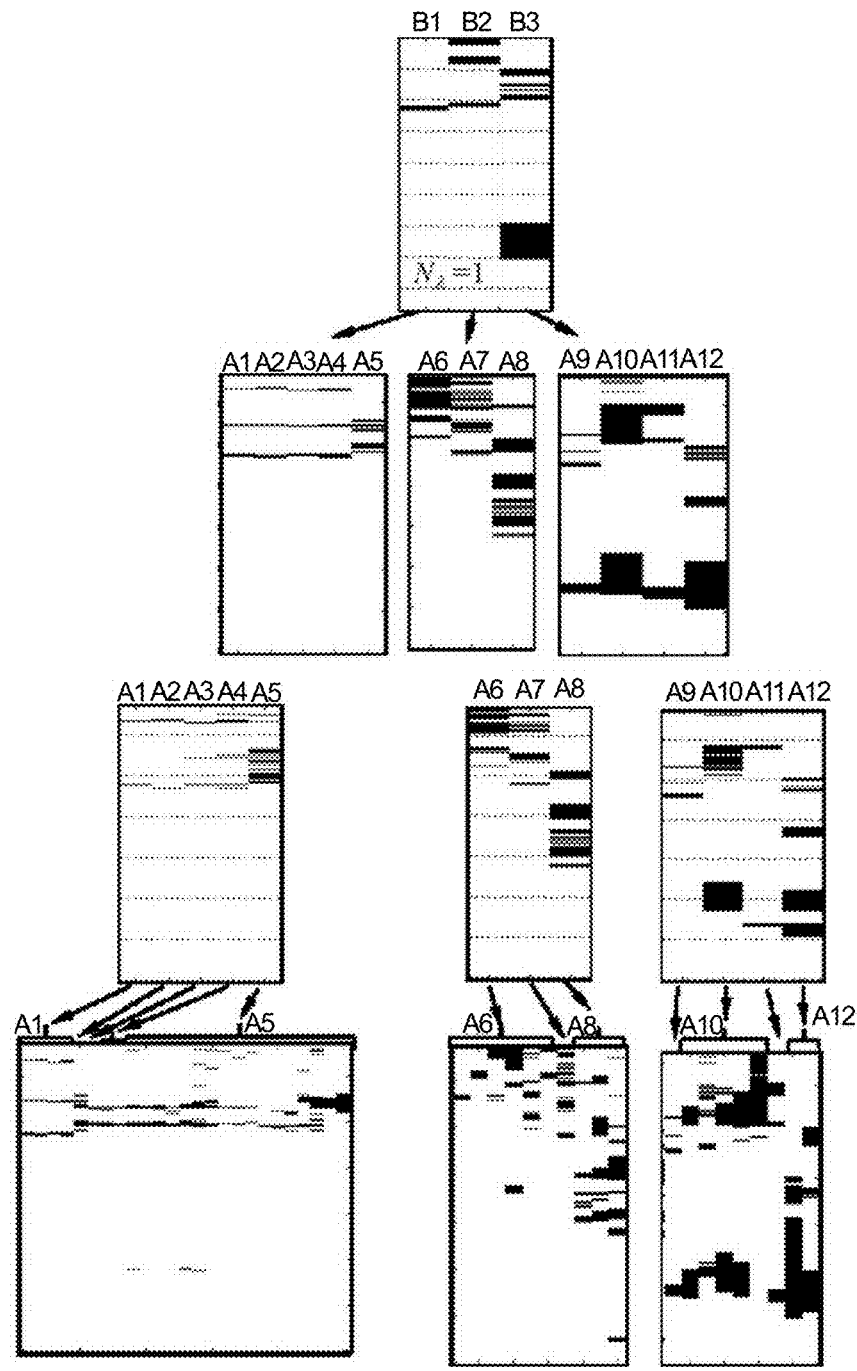

FIGS. 11A, 11B and 11C show those terminal-node and prototype intermediate node spectra from FIG. 8 after an exponential transformation is applied to each spectrum. Such a transformation highlights the stronger spectral peaks. In some cases, it is beneficial to probe at those wavenumbers corresponding to the spectral peaks of the anticipated chemicals that may be in the residue. The analog or colored or gray-scale representation of the spectra can be converted into binary representations by applying a threshold to the spectra, as illustrated in FIG. 11B. In this case, the threshold for each spectrum is set at one-half the value of the highest peak. The binary representation could be, for example, just a binary number or could represent the result of a determination of whether the output from the blind demixer 42 at a given wavenumber exceeds a threshold value.

Representing the reference spectra in binary form enables the sensor system to use logical operations to construct other prototype spectra for the various intermediate and higher-level nodes of the hierarchical structure. For example, FIG. 11C shows prototype spectra that are constructed by using a generalized exclusive OR (XOR) type operation on groups of underlying binary spectra of a cluster. In this example, if a cluster has two or three underlying spectra, a strict XOR is used. If a cluster has four to six underlying spectra, an XOR operation is used that permits at most two spectra to have a binary one value at the same wavenumber. If a cluster has more than six underlying spectra, an XOR operation is used that permits at most three spectra to have a binary one value at the same wavenumber. The wavenumber values at which the binary-logic defined prototype spectra such as these have a binary 1 value indicate the spectral points at which the observed spot can be probed to facilitate discrimination between the various underlying spectra of the cluster defined by the node with that prototype spectrum.

The plots of prototype spectra shown with a linear scale in FIG. 8 highlight the similarities between the underlying spectra, since that is the basis for their grouping into clusters. In contrast, the prototype spectra shown in FIG. 11C highlight the differing wavenumber locations of the multiple spectral peaks in the underlying spectra. Prototype spectra like those shown in FIG. 11C can be used to select the wavenumber values of a subsequent spectral measurement that is intended to enable the sensor system to distinguish between the various chemicals associated with those different underlying spectra. As an example, consider a case in which an initial spectral measurement has determined that chemicals in the probed area are likely members of the B2 cluster of the hierarchical organization. The wavenumbers indicated in the prototype spectrum of FIG. 11C for node B2 would be selected and the controller would control the spectrometer to illuminate the spot being probed with light of that combination of wavenumbers. The measured spectra would then be compared with the prototype spectra shown in FIG. 8 for nodes A6, A7 and A8 to determine the best match. If we then assume that the chemicals in the probed spot are likely members of the A6 sub-cluster, the wavenumbers indicated in the prototype spectrum of A6 would then be selected for the subsequent probing of the same spot.

When binary representations of the reference and prototype spectra and also of the demixed spectra are used for selecting the wavenumbers to use in probing a residue, it still may be beneficial to use the analog representations of those spectra when determining the chemical components in a region probed. Also, different spectral pre-processing, such as thresholding and calculation of derivatives or slopes and curvatures, can be applied when accomplishing the selection of wavenumbers in the probing light and when accomplishing the determination of the chemical components in a region probed.

Figure 12:
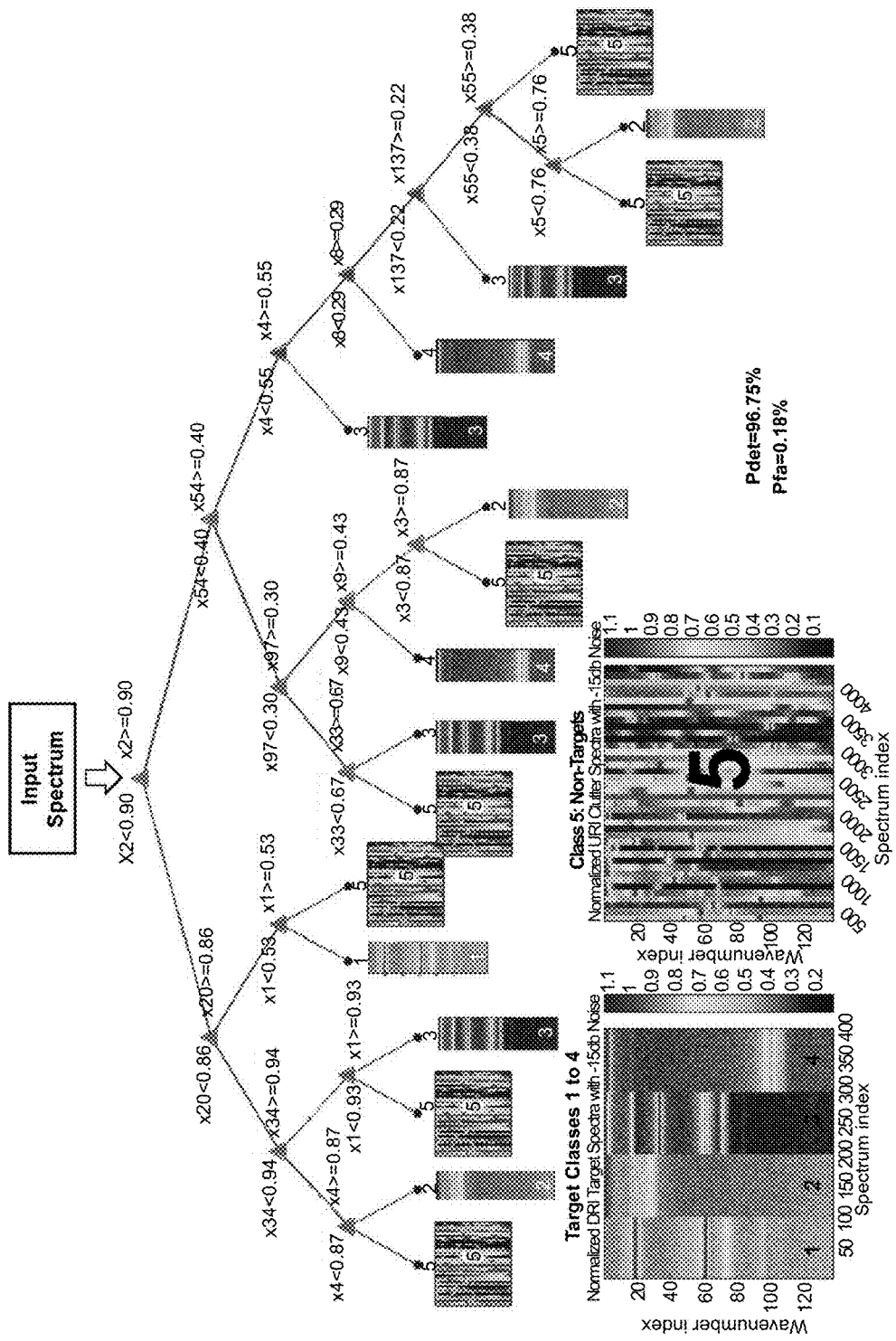
FIG. 12 shows an example of a decision tree constructed to identify 4 potential target spectra out of a total of 44 possible reference spectra in accordance with the present disclosure.

Other library organizations, such as a decision tree, can also be used to select the wavenumbers for probing a residue to determine its chemical constituents. FIG. 12 shows a decision tree that is constructed to identify 4 target chemicals selected from the same set of 44 reference spectra of FIG. 9, with the remaining 40 chemicals considered as clutter that do not need to be identified individually. The decision nodes on this exemplary decision tree consider whether the intensity value at a given wavenumber point is less than a threshold value or is greater than or equal to that threshold value. The specific wavenumber point and the threshold value considered at each decision node are indicated in FIG. 12. These decisions separate the 4 target components from each other and also from the clutter, which could be any combination of some of the other 40 chemicals.

The decision tree performs only classification of chemical components and depends on some other operations in the framework, such as the blind demixing ICA algorithm, to suitably separate or demix the measured spectral data into sets of data associated with a single chemical component, (i.e., the sample spectrum is of a single component and not of a mixture). Multiple sample spectra can be produced by the demixing algorithm. The data in the sample spectrum are then considered by the decision nodes of the decision tree. For the example shown in FIG. 12, the highest level of measurements, as indicated by the green triangles, are done at wavenumber index values x=2, 20, 54 and 97 (there are a total of 138 possible wavenumber points in this case). The spectral measurements at the next level are grouped into 3 sets, as indicated by the gray, gold and red triangles. The gray set includes wavenumber index values x=1, 4 and 34. The gold set includes wavenumber index values x=3, 9 and 33. The red set includes wavenumber index values x=4, 8 and 137. A lower level of spectral measurements is indicated by the blue triangles. The blue set includes wavenumber index values x=5 and 55. For the highest level, the wavenumbers selected are distributed fairly evenly among the spectral range. For the other levels, groupings of wavenumbers do not include immediately adjacent indices, in this example. Note that in other examples, it may be preferable to probe a residue with wavenumbers that are spaced as closely as achievable by the spectrometer.

The sequences of decisions made by following a path in a decision tree should end in a terminal node that is associated with a particular target component (1, 2, 3 or 4) or that is associated with the clutter (target class 5). It can be seen in FIG. 12 that target 1 is associated with only one terminal node but targets 2, 3 and 4 are associated with multiple terminal nodes. As might be expected, many terminal nodes are associated a compound considered as clutter. Many of the final decisions in the tree involve distinguishing between a particular target compound and clutter. It is evident from this exemplary tree that the targets which have their main spectral peaks occur at approximately the same wavenumber as other targets are present in more clusters of the tree structure.

FIGS. 13A, 13B, 13C, 13D, 13E, 13F, 13G, 13H and 13I illustrate how the decision tree of FIG. 12 can guide the selection of the wavenumber points used in successive spectral measurements of a ROI. It is assumed that the residue contains a mixture of target compounds 3 and 4 plus an additional compound that is considered as clutter, and labeled as spectrum 5. The first spectral measurement includes the wavenumbers in the green set (x=2, 20, 54 and 97), is illustrated in FIG. 13A. These spectral points measured at multiple spots in the ROI are provided by the controller to the blind demixing algorithm (e.g. ICA). The blind demixing algorithm separates the data into two sample spectra: Sample Spectrum 1a and Sample Spectrum 1b. For Sample Spectrum 1a, the decision tree is used by the system to evaluate that spectrum and arrive at the node indicated by the second arrow shown in FIG. 13B. The controller then specifies the second set of spectral measurements to be made using the gray set of wavenumbers (x=1, 4 and 34) and directs the spectrometer to again probe the ROI with that set of wavenumbers, as illustrated in FIG. 13C. The combined spectral measurements for both the green and gray wavenumbers are then supplied by the framework to the blind demixing algorithm. This algorithm produces a sample spectrum: Sample Spectrum 11a. The system then uses the decision tree to evaluate that sample spectrum and following the decisions indicated by the additional arrows in FIG. 13D arrives at the terminal node corresponding to target compound 3.

Next, the sensor system considers Sample Spectrum 1b. The sensor system again uses the decision tree to evaluate that spectrum and arrive at the node indicated by the third arrow shown in FIG. 13E. The controller then directs another set of spectral measurements to be made using the gold set of wavenumbers (x=3, 9 and 33) and directs the spectrometer to again probe the ROI with that set of wavenumbers, as illustrated in FIG. 13F. The combined spectral measurements for both the green and gold wavenumbers are then supplied by the framework to the blind demixer 42. In this example, the blind demixer 42 produces three sample spectra: Sample Spectrum 12a, Sample Spectrum 12b, and Sample Spectrum 12c. The system first uses the decision tree to evaluate Sample Spectrum 12a and following the decisions indicated by the additional arrows shown in FIG. 13G arrives at a terminal node with label 5, indicating that the sample spectrum corresponds to one or more of the clutter chemicals. The system then uses the decision tree to evaluate Sample Spectrum 12b and following the decisions indicated by the additional arrows shown in FIG. 13H arrives at a terminal node indicating that the sample spectrum corresponds to target compound 4. Finally, the system then uses the decision tree to evaluate Sample Spectrum 12c and following the decisions indicated by the additional arrows in FIG. 13I arrives at a terminal node indicating that the sample spectrum corresponds to target compound 3.

This example illustrates the effect of combining the wavenumber points obtained from multiple spectral measurements. When only the data for the green set of wavenumbers is available, the blind demixing algorithm is able to separate out a sample spectrum that isolates target compound 3 but could not separate target compound 4 from the clutter compound 5. However, when data at both the green and gold sets of wavenumbers are available, the blind demixing algorithm is able to separate target compound 4 from the clutter compound, and also separate target compound 3. When only the decision tree is used to identify the chemicals in a ROI, the sensor system depends entirely on the blind demixing algorithm to sufficiently separate the chemical constituents in a mixture.

The cluster-organized decision tree hierarchical structure can be used in combination with the blind demixing algorithm and with a non-blind modeling and classification algorithm (such as SRC) to detect and identify the chemicals constituents in mixtures. SRC is able to further demix a sample spectrum if that sample spectrum can be described as a linear combination of the reference spectra associated with the terminal nodes in one or more clusters specified by the sensor controller to the SRC algorithm. Such a combination is useful when the decision tree is quite complicated and has clusters with many branches and nodes.

In some embodiments, the sensor system organizes the library of reference spectra in both a decision tree structure and also some other hierarchical structure, such as one based on similarity in the wavenumber location of spectral peaks as well as in the shape (curvature) or other properties of those spectral peaks. The system can then use both library structures to make determinations of the chemical content of a residue ROI and compare the confidence weights of the results obtained with each of those two library structures and the sequences of spectral measurements determined by these library structures to arrive at a final identification of the chemical components in a probed region.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A sensor system comprising:
   a spectrometer with a light source having a plurality of selectable wavelengths;
   a controller for controlling the sensor system, for selecting wavelengths of illumination light produced by the light source, and for controlling the light source to illuminate a spatial location;
   a photodetector aligned to detect light received from the spatial location;
   a blind demixer coupled to the photodetector for separating received spectra in the detected light into a set of sample spectra associated with different chemical components;
   a background spectrum remover coupled to the photodetector and to blind demixer, the background spectrum remover capable of removing from the received spectra spectra known to be associated with spectral clutter;
   a memory having a plurality of stored reference spectra;
   a non-blind demixer coupled to the blind demixer and to the memory for non-blind demixing of the sample spectra using the reference spectra; and
   a classifier coupled to the non-blind demixer for classifying the set of demixed sample spectra into chemical components using the reference spectra.

2. The sensor system of claim 1:
   wherein the controller controls the sensor system to probe an area with illumination light with coarsely spaced wavelengths to distinguish between regions of interest containing residues and residue free background regions;
   wherein the classifier is coupled to the controller and controls the sensor system to probe the regions of interest with illumination light having wavelengths having a finer spacing than the coarsely spaced wavelengths to determine the chemical components in the regions of interest.

3. The sensor system of claim 1 wherein the blind demixer comprises an independent component analysis (ICA) algorithm.

4. The sensor system of claim 1 wherein the classifier comprises a sparse representation-based classification (SRC) algorithm.

5. The sensor system of claim 1 further comprising:
   a confidence-weighted chemical-identifier coupled to the classifier for determining confidence weights for the identified chemical components.

6. The sensor system of claim 5 further comprising:
   a known material comparer coupled to memory and to the confidence-weighted chemical-identifier for comparing the identified chemical components to known materials;
   wherein the known material comparer makes a final determination of the chemical component if the chemical component is a known material; and
   wherein the known material comparer updates the reference spectra in the memory if the chemical component is not a known material.

7. The sensor system of claim 1 wherein the spectral clutter is typically obtained in a measurement of a mixture of a chemical residue and a background material.

8. The sensor system of claim 1:
   wherein the controller controls the sensor system to probe an area with coarsely spaced wavelengths to distinguish between regions of interest that contain residues and background regions that are residue free;
   wherein the controller controls the sensor system to probe the regions of interest and the background regions with wavelengths having a finer spacing than the coarsely spaced wavelengths to determine the chemical components in the regions of interest and the background regions; and
   wherein the spectra determined to be spectral clutter in the background regions are removed from the received spectra of the regions of interest by the background spectrum remover.

9. The sensor system of claim 1:
   wherein the reference spectra comprise one or more of measurements of pure chemical residues, measurements of mixtures containing several chemical species, measurements of substrate materials, and measurements of spectral deformations resulting from various measurement conditions, including angle of illumination light, residue thickness, and texture.

10. A sensor system comprising:
    a spectrometer with a light source having a plurality of selectable wavelengths;
    a controller for controlling the sensor system, for selecting wavelengths of illumination light produced by the light source, and for controlling the light source to illuminate a spatial location;
    a photodetector aligned to detect light received from the spatial location;
    a blind demixer coupled to the photodetector for separating received spectra in the detected light into a set of sample spectra associated with different chemical components;
    a memory having a plurality of stored reference spectra;
    a non-blind demixer coupled to the blind demixer and to the memory for non-blind demixing of the sample spectra using the reference spectra; and a classifier coupled to the non-blind demixer for classifying the set of demixed sample spectra into chemical components using the reference spectra;

wherein the memory further comprises a stored hierarchically structured decision tree having a plurality of branches each coupled to a branch higher or lower in the hierarchically structured decision tree or to a termination leaf;

wherein a respective branch higher in the hierarchically structured decision tree has characteristics associated with lower branches or termination leafs coupled to the respective branch higher in the hierarchically structured decision tree; and wherein each termination leaf is associated with a respective reference spectrum.

11. A sensor system comprising:

a spectrometer with a light source having a plurality of selectable wavelengths;

a controller for controlling the sensor system, for selecting wavelengths of illumination light produced by the light source, and for controlling the light source to illuminate a spatial location;

a photodetector aligned to detect light received from the spatial location;

a blind demixer coupled to the photodetector for separating received spectra in the detected light into a set of sample spectra associated with different chemical components;

a memory having a plurality of stored reference spectra;

a non-blind demixer coupled to the blind demixer and to the memory for non-blind demixing of the sample spectra using the reference spectra; and a classifier coupled to the non-blind demixer for classifying the set of demixed sample spectra into chemical components using the reference spectra;

wherein the memory further comprises a stored hierarchically clustered spectral library;

wherein a cluster in the hierarchically clustered spectral library is formed by measuring each reference spectra and constructing an N-dimensional vector associated with each reference spectrum, wherein a length of a vector in each of N-dimensions of an N-dimensional vector is a value of the spectral intensity at a measured wavenumber; and wherein reference spectra having N-dimensional vectors whose Euclidean distance is not greater than a threshold are grouped in the same cluster.

12. A sensor system comprising: a spectrometer with a light source having a plurality of selectable wavelengths;

a controller for controlling the sensor system, for selecting wavelengths of illumination light produced by the light source, and for controlling the light source to illuminate a spatial location;

a photodetector aligned to detect light received from the spatial location;

a blind demixer coupled to the photodetector for separating received spectra in the detected light into a set of sample spectra associated with different chemical components;

a memory having a plurality of stored reference spectra;

a non-blind demixer coupled to the blind demixer and to the memory for non-blind demixing of the sample spectra using the reference spectra; and a classifier coupled to the non-blind demixer for classifying the set of demixed sample spectra into chemical components using the reference spectra;

a plurality of transmitter units, wherein each of the transmitter units simultaneously transmits a light beam having one of the plurality of selectable wavelengths; and an optical system coupled to the plurality of transmitter units and the photodetector, wherein the optical system directs the light beam from each of the transmitter units onto the illuminated spot, and wherein the optical system collects light from the illuminated spot and directs the light to the photodetector.

13. A method for detecting and identifying chemical components, the method comprising:

transmitting to a spatial location light having a first plurality of simultaneously occurring wavelengths;

measuring an intensity of back-scattered light from the first set of the plurality of simultaneously occurring wavelengths;

removing from the measured intensity of the back-scattered light from the first plurality of simultaneously occurring wavelengths spectra known to be associated with spectral clutter;

using the measured intensity of the back-scattered light to make an intermediate identification of the chemical components at the spatial location;

using the intermediate identification to determine a second a plurality of simultaneously occurring wavelengths for illuminating the spatial location, wherein the second plurality of simultaneously occurring wavelengths has a finer wavelength spacing than the first plurality of simultaneously occurring wavelengths;

transmitting to the spatial location light having the second plurality of simultaneously occurring wavelengths;

measuring an intensity of second back-scattered light from the second set of the plurality of simultaneously occurring wavelengths; and using the measured intensity of the second back-scattered light to make an identification of the chemical components at the spatial location.

14. The method of claim 13 further comprising:

using a plurality of reference spectra to determine the second set of the plurality of wavelengths.

15. The method of claim 14 wherein using the measured intensity of the second back-scattered light to make an identification of the chemical components comprises:

non-blind demixing and classification using the plurality of reference spectra;

wherein the reference spectra comprise one or more of measurements of pure chemical residues, measurements of mixtures containing several chemical species, measurements of substrate materials, and measurements of spectral deformations resulting from various measurement conditions, including angle of illumination light, residue thickness, and texture.

16. The method of claim 14 further comprising:

comparing the identified chemical components to known materials;

making a final determination of the chemical component if the chemical component is a known material; and updating the reference spectra if the chemical component is not a known material.

17. The method of claim 13 wherein using the measured intensity of the back-scattered light to make an intermediate identification of the chemical components comprises:

blind demixing.

18. The method of claim 13 wherein using the measured intensity of the second back-scattered light to make an identification of the chemical components comprises:

non-blind demixing and classification using a sparse representation-based classification (SRC) algorithm.

19. The method of claim 13 further comprising:
controlling a sensor system to probe an area with illumination light with coarsely spaced wavelengths to distinguish between regions of interest containing residues and residue free background regions;
controlling the sensor system to probe the regions of interest and the background regions with wavelengths having a finer spacing than the coarsely spaced wavelengths to determine the chemical components in the regions of interest and the background regions; and
removing spectra determined to be spectral clutter in the background regions from the received spectra of the regions of interest.

20. The method of claim 13 further comprising:
determining confidence weights for the identified chemical components.

21. The method of claim 13 wherein the spectral clutter is typically obtained in a measurement of a mixture of a chemical residue and a background material.

22. A method for detecting and identifying chemical components, the method comprising:
transmitting to a spatial location light having a first plurality of simultaneously occurring wavelengths;
measuring an intensity of back-scattered light from the first plurality of simultaneously occurring wavelengths;
using the measured intensity of the back-scattered light to make an intermediate identification of the chemical components at the spatial location;
using the intermediate identification to determine a second plurality of simultaneously occurring wavelengths for illuminating the spatial location, wherein the second plurality of simultaneously occurring wavelengths has a finer wavelength spacing than the first plurality of simultaneously occurring wavelengths;
transmitting to the spatial location light having the second plurality of simultaneously occurring wavelengths;
measuring an intensity of second back-scattered light from the second plurality of simultaneously occurring wavelengths; and
using the measured intensity of the second back-scattered light to make an identification of the chemical components at the spatial location;
using a hierarchically structured decision tree having a plurality of branches each coupled to a branch higher or lower in the hierarchically structured decision tree or to a termination leaf;
wherein a respective branch higher in the hierarchically structured decision tree has characteristics associated with lower branches or termination leafs coupled to the respective branch higher in the hierarchically structured decision tree; and
wherein each termination leaf is associated with a respective reference spectrum.

23. A method for detecting and identifying chemical components, the method comprising:
transmitting to a spatial location light having a first plurality of simultaneously occurring wavelengths;
measuring an intensity of back-scattered light from the first plurality of simultaneously occurring wavelengths;
using the measured intensity of the back-scattered light to make an intermediate identification of the chemical components at the spatial location;
using the intermediate identification to determine a second plurality of simultaneously occurring wavelengths for illuminating the spatial location, wherein the second plurality of simultaneously occurring wavelengths has a finer wavelength spacing than the first plurality of simultaneously occurring wavelengths;
measuring an intensity of second back-scattered light from the second plurality of simultaneously occurring wavelengths; and
using the measured intensity of the second back-scattered light to make an identification of the chemical components at the spatial location
using a hierarchically clustered spectral library;
wherein a cluster in the hierarchically clustered spectral library is formed by measuring a plurality of reference spectra and constructing an N-dimensional vector associated with each reference spectrum, wherein a length of a vector in each of N-dimensions of an N-dimensional vector is a value of the spectral intensity at a measured wavenumber; and
wherein reference spectra having N-dimensional vectors whose Euclidean distance is not greater than a threshold are grouped in the same cluster.

* * * * *